US010440953B2

(12) United States Patent
Gockel et al.

(10) Patent No.: US 10,440,953 B2
(45) Date of Patent: *Oct. 15, 2019

(54) CONTROL OF PESTS IN MAIZE BY GINKGOLIDES AND BILOBALIDE

(71) Applicant: BASF SE, Ludwigshafen am Rhein (DE)

(72) Inventors: Birgit Gockel, Ludwigshafen (DE); Joachim Dickhaut, Heidelberg (DE); Daniel Saelinger, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/749,823

(22) PCT Filed: Aug. 5, 2016

(86) PCT No.: PCT/EP2016/068729
§ 371 (c)(1),
(2) Date: Feb. 2, 2018

(87) PCT Pub. No.: WO2017/025454
PCT Pub. Date: Feb. 16, 2017

(65) Prior Publication Data
US 2018/0220656 A1 Aug. 9, 2018

(30) Foreign Application Priority Data

Aug. 7, 2015 (EP) .................................... 15180235

(51) Int. Cl.
C07D 307/94 (2006.01)
C07D 493/10 (2006.01)
A01N 43/12 (2006.01)
A01N 43/90 (2006.01)

(52) U.S. Cl.
CPC .................................... A01N 43/90 (2013.01)

(58) Field of Classification Search
None
See application file for complete search history.

(56) References Cited

U.S. PATENT DOCUMENTS

| 5,700,468 | A | 12/1997 | Bombardelli et al. | |
|---|---|---|---|---|
| 2011/0110906 | A1* | 5/2011 | Andersch | A01N 63/00 424/93.46 |
| 2014/0073592 | A1 | 3/2014 | Pszczolkowski et al. | |
| 2016/0297793 | A1 | 10/2016 | Bandur et al. | |
| 2016/0318897 | A1 | 11/2016 | Koerber et al. | |
| 2016/0326153 | A1 | 11/2016 | Koerber et al. | |
| 2016/0345581 | A1 | 12/2016 | Soergel et al. | |
| 2016/0366889 | A1* | 12/2016 | Salinger | A01N 43/90 |
| 2017/0036969 | A1 | 2/2017 | Nave et al. | |
| 2017/0181435 | A1 | 6/2017 | Nave et al. | |
| 2017/0210712 | A1 | 7/2017 | Gockel et al. | |
| 2017/0223964 | A1 | 8/2017 | Nave et al. | |
| 2017/0238554 | A1 | 8/2017 | Saelinger et al. | |
| 2017/0313631 | A1 | 11/2017 | Nave et al. | |
| 2018/0016199 | A1 | 1/2018 | Nave et al. | |

FOREIGN PATENT DOCUMENTS

| CN | 1398524 A | 2/2003 | |
|---|---|---|---|
| CN | 102379296 A | 3/2012 | |
| EP | 0360556 A1 | 3/1990 | |
| EP | 0431535 A1 | 6/1991 | |
| EP | 2762003 A1 | 8/2014 | |
| JP | H09110713 A | 4/1997 | |
| JP | 2008162920 A | 7/2008 | |
| KR | 20140040896 A | 4/2014 | |
| WO | 2005025587 A1 | 3/2005 | |
| WO | WO-2005025587 A1 * | 3/2005 | ............ A01N 43/90 |
| WO | 2015022293 A1 | 2/2015 | |
| WO | 2015055497 A1 | 4/2015 | |
| WO | 2015086790 A1 | 6/2015 | |
| WO | 2015092575 A1 | 6/2015 | |
| WO | 2015104699 A2 | 7/2015 | |
| WO | 2015104700 A2 | 7/2015 | |
| WO | 2015124606 A1 | 8/2015 | |
| WO | 2015124706 A1 | 8/2015 | |
| WO | 2015128338 A1 | 9/2015 | |
| WO | 2015162133 A1 | 10/2015 | |
| WO | 2015162244 A1 | 10/2015 | |
| WO | 2015165960 A1 | 11/2015 | |
| WO | 2015169734 A1 | 11/2015 | |
| WO | 2015189080 A1 | 12/2015 | |
| WO | 2016055431 A1 | 4/2016 | |
| WO | 2016062678 A1 | 4/2016 | |
| WO | 2016062680 A1 | 4/2016 | |
| WO | 2016097318 A1 | 6/2016 | |
| WO | 2016113261 A1 | 7/2016 | |
| WO | 2016113271 A1 | 7/2016 | |
| WO | 2016180859 A1 | 11/2016 | |
| WO | 2016198611 A1 | 12/2016 | |
| WO | 2016198613 A1 | 12/2016 | |
| WO | 2016202807 A1 | 12/2016 | |

OTHER PUBLICATIONS

Grbíc et al., "The genome of Tetranychus urticae reveals herbivorous pest adaptations," Nov. 24, 2011, vol. 479, Nature 487.*
Gao et al., "Characterization of Cry34Ab1 and Cry35Ab1 Insecticidal Crystal Proteins Expressed in Transgenic Corn Plants and Pseudomonas fluorescens," J. Agric. Food Chem. 2004, 52, 8057-8065.*
Lee et al., "Repellent and Pesticidal Effect of Ginkgo biloba Leaves Extracts on the Tetranichus urticae, Aphis gossypii and Myzus persicae," J. Korean Soc. Appl. Biol. Chem. 48(2), 150-154 (2005).*
Reddy et al., "Herbicide resistant crops: History, development and current technologies," Indian Journal of Agronomy 57(1):1-7, Mar. 2012.*

(Continued)

Primary Examiner — Jared Barsky
(74) Attorney, Agent, or Firm — Armstrong Teasdale LLP

(57) ABSTRACT

Described herein is a method for controlling pests of a maize plant, including the step of contacting the maize plant, parts of the maize plant, or its propagation material with components of the ginkgo tree selected from bilobalide, ginkgolide A, ginkgolide B, ginkgolide C, ginkgolide J, ginkgolide M, and mixtures thereof. Further described herein is the use of the components of the ginkgo tree for controlling pests on the maize plant, parts of the maize plant, or its plant propagation material.

13 Claims, No Drawings

(56) References Cited

OTHER PUBLICATIONS

Li et al., "Bt maize expressing Cry3Bb1 does not harm the spider mite, *Tetranychus urticae*, or its ladybird beetle predator, *Stethorus punctillum*," Biological Control 53 (2010) 337-344.*
Stål et al., "Brown Marmorated Stink Bug as a Pest of Corn and Soybeans," Penn State College of Agricultural Sciences, Entomological Notes, Dec. 2012.*
Bessin, "Bt-Corn for Border Control," UK Cooperative Extension Service, published Revised Nov. 2010.*
International Search Report and Written Opinion for International Application No. PCT/EP2016/068729, dated Sep. 22, 2016, 11 pages.
M. O'Day et al: "Corn Insect Pests: A Diagnostic Guide", Jan. 1, 1998, pp. 1-52, XP055216395.
Van Beek T A Ed—Chankvetadze B et al.L "Chemical analysis of Ginkgo biloba leaves and extracts", Journal of Chromatography, vol, 967, No. 1, Aug. 16, 2002, pp. 21-55, XP004372044.
Ahn, et al., "Potent Insecticidal Activity of Ginkgo biloba Derived Trilactone Terpenes Against Nilaparvata lugens", Phytochemicals for Pest Control, vol. 658, Chapter 7, Mar. 19, 1997, pp. 90-105.
European Search Report for EP Patent Application No. 15180235.2, Completed on Sep. 30, 2015, 3 pages.

* cited by examiner

CONTROL OF PESTS IN MAIZE BY GINKGOLIDES AND BILOBALIDE

CROSS-REFERENCE TO RELATED APPLICATIONS

This application is a U.S. National Phase Application of International Patent Application No. PCT/EP2016/068729, filed Aug. 5, 2016, which claims the benefit of priority to European Patent Application No. 15180235.2, filed Aug. 7, 2015, the entire contents of which are hereby incorporated by reference herein.

FIELD OF THE INVENTION

The invention relates to a method for controlling pests of a maize plant, comprising the step of contacting the maize plant, parts of it, or its propagation material, the pests, their food supply, habitat, or breeding grounds with components of the ginkgo tree selected from bilobalide, ginkgolide A, ginkgolide B, ginkgolide C, ginkgolide J and ginkgolide M, and mixtures thereof. The invention also relates to the use of one, or more components of the ginkgo tree selected from bilobalide, ginkgolide A, ginkgolide B, ginkgolide C, ginkgolide J and ginkgolide M, and mixtures thereof, for controlling pests in maize plants. Maize (*Zea mays*, corn) is an important commercial crop plant in many countries and constitutes a high percentage of total production of nutrients on the American continent. Maize is not only relevant for direct human consumption, but also for nutrition of farmed animals, and for production of renewable energy. The damages caused by insects on maize harvests, e.g. insects from the superfamilies of Pentatomidae—comprehensively referred to as stink bugs—and/or Thripidae, represents a huge economical risk to the farmer. Evaluations of losses of corn in the state of Georgia (US) ranked stinkbugs as one of the most damaging insects for corn (Guillebeau, Hille, Roberts, Summary of Losses from Insect Damage and Cost of Control in Georgia 2005). Stinkbugs (especially *Dichelops furcatus* and *Dichelops melacanthus*) also pose huge challenges for maize farmers in south American countries like Brazil, where their populations have exploded after the shift from conventional tillage to the no tillage cultivation system (Silva et al., Neotrop Entomol. 2013, 42(2), 141-145). Thripidae are also of exceptional relevance to infestation of maize plants, e.g. by *Frankliniella* spp., which occurs on seeds, seedlings and young plants, as well as on ears, where they infest the kernel and open infection pathways for other pathogens (UC IPM Pest Management Guidelines: Corn, 2011). *Frankliniella occidentalis*, and *Frankiniella williamsi* represent some of the most aggressive pests on maize. Once constrained to several areas in the US, they have spread worldwide in the past years. The family of Pentatomidae comprises *Euschistus* spp., *Halyomorpha* spp., *Dichelops* spp., *Nezara* spp. and/or *Oebalus* spp., all being of extraordinary relevance on maize plants (Venugopal et al., Plos One 2014, Vol. 9(10); Tillman, Environmental Entymology, 2011, 1159-1176; Tillman, Environmental Entymology, 2010, 1184-1194). These families infest young maize plants and feed on the fresh leaves, thereby considerably weakening the plant, killing seedlings, and delaying development of crops (Clower D F. Damage to corn by the southern green stink bug. Journal of Economic Entomology, 1958, 51, 471-473). Typical species found in maize are *Euschistus servus* (brown stink bug), *Euschistus heros* (Neotropical brown stink bug), *Halyomorpha halys* (brown marmorated stink bug), *Dichelops furcatus*, *Dichelops melacanthus*, *Nezara viridula* (southern green stink bug), and *Oebalus pugnax* (rice stink bug). Insecticides commonly used to control stinkbugs include pyrethroids, neonicotinoids and organophosphates. However, there are increasing problems with insecticide resistance, particularly in brown stink bug populations and particularly to pyrethroids. *Euschistus heros* can also be difficult to manage using organophosphates, or endosulfan (Sosa-Gomez et al., 2009). There is therefore a need for effective methods of controlling stinkbugs in maize, especially for overcoming resistance problems. Furthermore, the stricter regulatory requirements on pesticides causes a need for pesticides with lower toxicities, and enhanced environmental safety, e.g. lower pesticide residues, higher target selectivity, reduced impact on non-pest animals (e.g. bees), improved aquatic safety, and reduced dose rates. On top, there is a need for pesticides that are able to control pests that have become resistant to insecticidal traits of genetically modified maize plants.

BACKGROUND

Ginkgolides and bilobalide are natural products that are produced by the Ginkgo tree. An acaricidal activity of ginkgolide C is disclosed in CN 102379296 (A). WO 2005/025587 discloses an insecticidal activity of mixtures of ginkgolide A, B and bilobalide against two spotted spider mites and green peach aphid. WO2015/128338 discloses uses and methods of application of ginkgolides and bilobalide against Pentatomidae and/or Thripidae on Faboidae.

DETAILED DESCRIPTION

In view of the importance of maize in agriculture, it was an objective to supply uses and methods of application for pest control in maize, especially of pests selected from Pentatomidae, and Thripidae, and in particular of pests that have become resistant to another insecticide, or an insecticidal trait of a genetically modified maize plant. It has now surprisingly been found that ginkgolides and/or bilobalide selected from bilobalide, ginkgolide A, ginkgolide B, ginkgolide C, ginkgolide J and ginkgolide M, or mixtures thereof, are exceptionally suitable to address the above problems and needs. These compounds therefore represent an important solution for controlling pests of maize, especially pests from the families of Pentatomidae and/or Thripidae, and thereby safeguarding plants, and propagation material from the infestation by such pests, particularly where the pests have become resistant to other insecticides, or insecticidal traits of genetically modified plants. In particular, it has surprisingly been found that the application of these compounds on maize plants having insecticidal traits is highly effective for combating pests on these maize plants, such as pests that have become resistant to the insecticidal traits.

Bilobalide and the ginkgolides are known components of the ginkgo tree having the following structures:

a) Bilobalide:

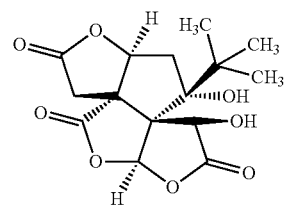

Bilobalide is the common name for (3aS,5aR,8aS,9R,10aR)-9-tert-butyl-8,9-dihydroxydihydro-9H-furo[2,3-b]furo[3',2';2,3]cyclopenta[1,2-c]furan-2,4,7(3H,8H)-trione (CAS 33570-04-6).

b) Ginkgolides:

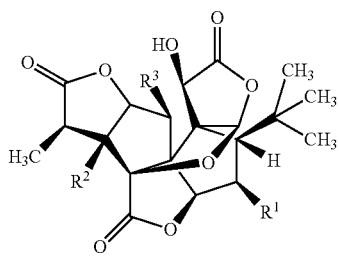

TABLE A

Definitions of substituents for Ginkgolides

| Ginkgolide | $R^1$ | $R^2$ | $R^3$ | CAS |
|---|---|---|---|---|
| Ginkgolide A | H | OH | H | 15291-75-5 |
| Ginkgolide B | H | OH | OH | 15291-77-7 |
| Ginkgolide C | OH | OH | OH | 15291-76-6 |
| Ginkgolide J | OH | OH | H | 15291-79-9 |
| Ginkgolide M | OH | H | OH | 15291-78-8 |

The compounds of Table A can be used in pure form, as mixtures, or in the form of extracts of ginkgo leaves, which may be enriched with the above compounds to a certain degree. The components of the ginkgo tree in Table A are also referred to as "component(s) of the ginkgo tree". Accordingly, when referring to the component(s) of the ginkgo tree, the term relates to at least one of the compounds of Table A, or a mixture thereof.

The compounds are commercially available, or can be obtained, preferably from ginkgo leaves by methods known in the art and described e.g. in U.S. Pat. No. 5,700,468, EP-A 360 556, EP-A 0 431 535 and JP-A 09-110713. Further, the compounds bilobalide (in enantiopure form), ginkgolide A (in its racemic form) and ginkgolide B (in its racemic form) can be obtained by chemical synthesis, as disclosed e.g. in Tetrahedron Letters (1988), 29(28), 3423-6, Tetrahedron Letters (1988), 29(26), 3205-6 and Journal of the American Chemical Society (2000), 122(35), 8453-8463, respectively.

Within this application, combinations of embodiments and/or preferences with other embodiments and/or preferences are within the scope of the invention, regardless of the level of preference of the respective features.

The uses and methods disclosed herein relate to the application of bilobalide, ginkgolide A, ginkgolide B, ginkgolide C, ginkgolide J, ginkgolide M, or mixtures thereof. In one embodiment, the uses and methods relate to bilobalide and/or ginkgolide A, or mixtures thereof. In another embodiment, the uses and methods relate to bilobalide.

In another embodiment, the uses and methods relate to ginkgolide A. In another embodiment, the uses and methods relate to ginkgolide B. In another embodiment, the uses and methods of the invention relate to ginkgolide C. In another embodiment, the uses and methods of the invention relate to ginkgolide J. In another embodiment, the uses and methods of the invention relate to ginkgolide M.

The methods and uses of the invention are for controlling pests of a maize plant, preferably by Pentatomidae and/or Thripidae. In one embodiment, the methods and uses of the present invention are applied for controlling pests from the family of Pentatomidae. In another embodiment, the methods and uses of the present invention are applied for controlling pests from the family of Thripidae.

In one embodiment, the methods and uses of the present invention relate to a maize plant, which has been modified by conventional breeding, i.e. a plant, which has not been modified by mutagenesis, or genetic engineering. In another embodiment, the methods and uses of the present invention relate to a genetically modified maize plant. In another embodiment, the components of the ginkgo tree are applied for controlling pests that are resistant to one, or more other insecticides, preferably pyrethroids, neonicotinoids and organophosphates, and more preferably pyrethroid insecticides. In another embodiment, the components of the ginkgo tree are applied for controlling pests that are resistant to an insecticidal trait of a genetically modified plant.

The term "genetically modified" refers to mutagenesis, or genetic engineering techniques. In one embodiment, the term refers to mutagenesis. In another embodiment, the term refers to genetic engineering. In yet another embodiment, the term refers to a combination of genetic engineering with conventional breeding. In yet another embodiment, the term refers to a combination of mutagenesis with conventional breeding.

When used in connection with genetically modified plants, the term "mutagenesis" includes random mutagenesis by mutagens and directed mutagenesis, but does not include mutagenesis derived from natural events, e.g. meiosis.

The term "conventional breeding" refers to methods comprising crossing (i.e. utilizing meiosis) and/or selection, e.g. crossbreeding, mutagenesis (i.e. by natural events, such as meiosis, but excluding induction by mutagens, or directed mutagenesis), or recombination (such as sexual recombination, but excluding directed recombination by introduction of DNA fragments produced by methods of genetic engineering). Conventional breeding may include the application of selection markers, such as herbicide tolerance. Typical plants that are obtainable by conventional breeding are plants of the Clearfield™ product line, such as Clearfield™ maize. Such plants obtainable by conventional breeding may carry a herbicide tolerance, preferably against Imazethapyr, or Imazapyr. Usually, genetically modified plants as referred to in this application carry a gene of a different organism, which gene is also referred to as transgene. The skilled person is able to select suitable techniques to produce genetically modified plants, and to analyze plants on genetic modifications.

Maize plants that are "resistant" against insects display a lower degree of infestation by at least one insect species compared to a maize plant of the same variety. Such resistance may be achieved by conventional cultivation techniques, or by mutagenesis and/or genetic engineering. Pests that are "resistant" to a particular insecticide, or insecticidal trait of a maize plant are less sensitive to that insecticide, or insecticidal trait of a maize plant compared to the same pest species, in particular compared to the same subspecies. Accordingly, Pentatomidae that are "resistant" to a particular insecticide, or insecticidal trait of a maize plant refers e.g. to strains of Pentatomidae that are less sensitive to that insecticide, or insecticidal trait of a maize plant compared to the expected sensitivity of the same species of Pentatomidae. The expected sensitivity can be measured using e.g. a strain that has not previously been exposed to the insecticide, or the insecticidal trait of a genetically modified maize plant.

In one embodiment the components of the ginkgo tree are used to control and/or prevent infestation by Thripidae, preferably *Frankliniella* spp. (e.g. *Frankliniella occidentalis, Frankliniella williamsi*). In another embodiment, the components of the ginkgo tree are applied for controlling and/or preventing infestation by Pentatomidae selected from *Euschistus* spp., *Halyomorpha* spp., *Dichelops* spp., *Nezara* spp., or *Oebalus* spp. In yet another embodiment, the components of the ginkgo tree are applied for controlling and/or preventing infestation by Pentatomidae selected from *Euschistus* spp., *Halyomorpha* spp., *Dichelops* spp., or *Nezara* spp. In yet another embodiment, the components of the ginkgo tree are applied for controlling and/or preventing infestation by *Halyomorpha* spp., *Dichelops* spp., or *Oebalus* spp. In yet another embodiment, the components of the ginkgo tree are applied for controlling and/or preventing infestation by *Euschistus* spp. In yet another embodiment, the components of the ginkgo tree are applied for controlling and/or preventing infestation by *Halyomorpha* spp. In yet another embodiment, the components of the ginkgo tree are applied for controlling and/or preventing infestation by *Dichelops* spp. In yet another embodiment, the components of the ginkgo tree are applied for controlling and/or preventing infestation by *Nezara* spp. In yet another embodiment, the components of the ginkgo tree are applied for controlling and/or preventing infestation by *Oebalus* spp. In one embodiment, the components of the ginkgo tree are applied for controlling and/or preventing infestation by *Euschistus servus, Euschistus heros, Halyomorpha halys, Dichelops furcatus, Dichelops melacanthus, Nezara viridula*, or *Oebalus pugnax*. In another embodiment, the components of the ginkgo tree are applied for controlling and/or preventing infestation by *Euschistus servus, Halyomorpha halys, Dichelops furcatus, Dichelops melacanthus, Nezara viridula*, or *Oebalus pugnax*. In another embodiment, the components of the ginkgo tree are applied for controlling and/or preventing infestation by *Euschistus servus, Halyomorpha halys, Dichelops furcatus, Dichelops melacanthus*, or *Nezara viridula*. In yet another embodiment, the components of the ginkgo tree are applied for controlling and/or preventing infestation by *Halyomorpha halys, Dichelops furcatus, Dichelops melacanthus*, or *Oebalus pugnax*. In yet another embodiment, the components of the ginkgo tree are applied for controlling and/or preventing infestation by *Euschistus servus*. In yet another embodiment, the components of the ginkgo tree are applied for controlling and/or preventing infestation by *Euschistus heros*. In yet another embodiment, the components of the ginkgo tree are applied for controlling and/or preventing infestation by *Halyomorpha halys*. In yet another embodiment, the components of the ginkgo tree are applied for controlling and/or preventing infestation by *Dichelops furcatus*. In yet another embodiment, the components of the ginkgo tree are applied for controlling and/or preventing infestation by *Dichelops melacanthus*. In yet another embodiment, the components of the ginkgo tree are applied for controlling and/or preventing infestation by *Nezara viridula*. In yet another embodiment, the components of the ginkgo tree are applied for controlling and/or preventing infestation by *Oebalus pugnax*. In one embodiment, the uses and methods of the application relate to the *Oebalus* spp., preferably *Oebalus pugnax* in general, independent of a locus of application. In one embodiment, the application of the components of the ginkgo tree are applied to pests on maize plants. In another embodiment, the application of the components of the ginkgo tree are applied to pests of maize plants, independent of their locus. In another embodiment, the pests are animal pests such as arthropods, gastropods and nematodes including but not limited to: insects from the order of Lepidoptera, for example *Achroia grisella, Acleris* spp. such as *A. fimbriana, A. gloverana, A. variana; Acrolepiopsis assectella, Acronicta major, Adoxophyes* spp. such as *A. cyrtosema, A. orana; Aedia leucomelas, Agrotis* spp. such as *A. exclamationis, A. fucosa, A. ipsilon, A. orthogoma, A. segetum, A. subterranea; Alabama argiliacea, Aleurodicus dispersus, Alsophila pometaria, Ampelophaga rubiginosa, Amyelois transitella, Anacampsis sarcitella, Anagasta kuehniella, Anarsia lineatella, Anisota senatoria, Antheraea pernyi, Anticarsia (=Thermesia)* spp. such as *A. gemmatalis; Apamea* spp., *Aproaerema modicella, Archips* spp. such as *A. argyrospila, A. fuscocupreanus, A. rosana, A. xyloseanus; Argyresthia conjugella, Argyroploce* spp., *Argyrotaenia* spp. such as *A. velutinana; Athetis mindara, Austroasca viridigrisea, Autographa gamma, Autographa nigrisigna, Barathra brassicae, Bedellia* spp., *Bonagota salubricola, Borbo cinnara, Bucculatrix thurberiella, Bupalus piniarius, Busseola* spp., *Cacoecia* spp. such as *C. murinana, C. podana; Cactoblastis cactorum, Cadra cautella, Calingo braziliensis, Caloptilis theivora, Capua reticulana, Carposina* spp. such as *C. niponensis, C. sasakii; Cephus* spp., *Chaetocnema aridula, Cheimatobia brumata, Chilo* spp. such as *C. indicus, C. suppressalis, C. partellus; Choreutis pariana, Choristoneura* spp. such as *C. conflictana, C. fumiferana, C. longicellana, C. murinana, C. occidentalis, C. rosaceana; Chrysodeixis (=Pseudoplusia)* spp. such as *C. eriosoma, C. includens; Cirphis unipuncta, Clysia ambiguella, Cnaphalocerus* spp., *Cnaphalocrocis medinalis, Cnephasia* spp., *Cochylis hospes, Coleophora* spp., *Colias eurytheme, Conopomorpha* spp., *Conotrachelus* spp., *Copitarsia* spp., *Corcyra cephalonica, Crambus caliginosellus, Crambus teterrellus, Crocidosema (=Epinotia) aporema, Cydalima (=Diaphania) perspectalis, Cydia (=Carpocapsa)* spp. such as *C. pomonella, C. latiferreana; Dalaca noctuides, Datana integerrima, Dasychira pinicola, Dendrolimus* spp. such as *D. pini, D. spectabilis, D. sibiricus; Desmia funeralis, Diaphania* spp. such as *D. nitidalis, D. hyalinata; Diatraea grandiosella, Diatraea saccharalis, Diphthera festiva, Earias* spp. such as *E. insulana, E. vittella; Ecdytolopha aurantianu, Egira (=Xylomyges) curialis, Elasmopalpus lignosellus, Eldana saccharina, Endopiza viteana, Ennomos subsignaria, Eoreuma loftini, Ephestia* spp. such as *E. cautella, E. elutella, E. kuehniella; Epinotia aporema, Epiphyas postvittana, Erannis tiliaria, Erionota thrax, Etiella* spp., *Eulia* spp., *Eupoecilia ambiguella, Euproctis chrysorrhoea, Euxoa* spp., *Evetria bouliana, Faronta albilinea, Feltia* spp. such as *F. subterranean; Galleria mellonella, Gracillaria* spp., *Gracholita* spp. such as *G. funebrana, G. molesta, G. inopinata; Halysidota* spp., *Harrisina americana, Hedylepta* spp., *Helicoverpa* spp. such as *H. armigera (=Heliothis armigera), H. zea (=Heliothis zea); Heliothis* spp. such as *H. assulta, H. subflexa, H. virescens; Hellula* spp. such as *H. undalis, H. rogatalis; Helocoverpa gelotopoeon, Hemileuca oliviae, Herpetogramma licarsisalis, Hibernia defoliaria, Hofmannophila pseudospretella, Homoeosoma electellum, Homona magnanima, Hypena scabra, Hyphantria cunea, Hyponomeuta padella, Hyponomeuta malinellus, Kakivoria flavofasciata, Keiferia lycopersicella, Lambdina fiscellaria fiscellaria, Lambdina fiscellaria lugubrosa, Lamprosema indicata, Laspeyresia molesta, Leguminivora glycinivorella, Lerodea eufala, Leucinodes orbonalis, Leucoma salicis, Leucoptera* spp. such as *L. coffeella, L. scitella; Leuminivora lycinivorella, Lithoc-*

*olletis blancardella*, *Lithophane antennata*, *Llattia octo* (=*Amyna axis*), *Lobesia botrana*, *Lophocampa* spp., *Loxagrotis albicosta*, *Loxostege* spp. such as *L. sticticalis*, *L. cereralis*; *Lymantria* spp. such as *L. dispar*, *L. monacha*; *Lyonetia clerkella*, *Lyonetia prunifoliella*, *Malacosoma* spp. such as *M. americanum*, *M. californicum*, *M. constrictum*, *M. neustria*; *Mamestra* spp. such as *M. brassicae*, *M. configurata*; *Mamstra brassicae*, *Manduca* spp. such as *M. quinquemaculata*, *M. sexta*; *Marasmia* spp, *Marmara* spp., *Maruca testulalis*, *Megalopyge lanata*, *Melanchra picta*, *Melanitis leda*, *Mocis* spp. such as *M. lapites*, *M. repanda*; *Mocis latipes*, *Monochroa fragariae*, *Mythimna separata*, *Nemapogon cloacella*, *Neoleucinodes elegantalis*, *Nepytia* spp., *Nymphula* spp., *Oiketicus* spp., *Omiodes indicata*, *Omphisa anastomosalis*, *Operophtera brumata*, *Orgyia pseudotsugata*, *Oria* spp., *Orthaga thyrisalis*, *Ostrinia* spp. such as *O. nubilalis*; *Oulema oryzae*, *Paleacrita vernata*, *Panolis flammea*, *Parnara* spp., *Papaipema nebris*, *Papilio cresphontes*, *Paramyelois transitella*, *Paranthrene regalis*, *Paysandisia archon*, *Pectinophora* spp. such as *P. gossypiella*; *Peridroma saucia*, *Perileucoptera* spp., such as *P. coffeella*; *Phalera bucephala*, *Phryganidia californica*, *Phthorimaea* spp. such as *P. operculella*; *Phyllocnistis citrella*, *Phyllonorycter* spp. such as *P. blancardella*, *P. crataegella*, *P. issikii*, *P. ringoniella*; *Pieris* spp. such as *P. brassicae*, *P. rapae*, *P. napi*; *Pilocrocis tripunctata*, *Plathypena scabra*, *Platynota* spp. such as *P. flavedana*, *P. idaeusalis*, *P. stultana*; *Platyptilia carduidactyla*, *Plebejus argus*, *Plodia interpunctella*, *Plusia* spp, *Plutella maculipennis*, *Plutella xylostella*, *Pontia protodica*, *Prays* spp., *Prodenia* spp., *Proxenus lepigone*, *Pseudaletia* spp. such as *P. sequax*, *P. unipuncta*; *Pyrausta nubilalis*, *Rachiplusia nu*, *Richia albicosta*, *Rhizobius ventralis*, *Rhyacionia frustrana*, *Sabulodes aegrotata*, *Schizura concinna*, *Schoenobius* spp., *Schreckensteinia festaliella*, *Scirpophaga* spp. such as *S. incertulas*, *S. innotata*; *Scotia segetum*, *Sesamia* spp. such as *S. inferens*, *Seudyra subflava*, *Sitotroga cerealella*, *Sparganothis pilleriana*, *Spilonota lechriaspis*, *S. ocellana*, *Spodoptera* (=*Lamphygma*) spp. such as *S. eridania*, *S. exigua*, *S. frugiperda*, *S. latisfascia*, *S. littoralis*, *S. litura*, *S. omithogalli*; *Stigmella* spp., *Stomopteryx subsecivella*, *Strymon bazochii*, *Sylepta derogata*, *Synanthedon* spp. such as *S. exitiosa*, *Tecia solanivora*, *Telehin licus*, *Thaumatopoea pityocampa*, *Thaumatotibia* (=*Cryptophlebia*) *leucotreta*, *Thaumetopoea pityocampa*, *Thecla* spp., *Theresimima ampelophaga*, *Thyrinteina* spp, *Tildenia inconspicuella*, *Tinea* spp. such as *T. cloacella*, *T. pellionella*; *Tineola bisselliella*, *Tortrix* spp. such as *T. viridana*; *Trichophaga tapetzella*, *Trichoplusia* spp. such as *T. ni*; *Tuta* (=*Scrobipalpula*) *absoluta*, *Udea* spp. such as *U. rubigalis*, *U. rubigalis*; *Virachola* spp., *Yponomeuta padella*, and *Zeiraphera canadensis*; insects from the order of Coleoptera, for example *Acalymma vittatum*, *Acanthoscehdes obtectus*, *Adoretus* spp., *Agelastica alni*, *Agrilus* spp. such as *A. anxius*, *A. planipennis*, *A. sinuatus*; *Agriotes* spp. such as *A. fuscicollis*, *A. lineatus*, *A. obscurus*; *Alphitobius diaperinus*, *Amphimallus solstitialis*, *Anisandrus dispar*, *Anisoplia austriaca*, *Anobium punctatum*, *Anomala corpulenta*, *Anomala rufocuprea*, *Anoplophora* spp. such as *A. glabripennis*; *Anthonomus* spp. such as *A. eugenii*, *A. grandis*, *A. pomorum*; *Anthrenus* spp., *Aphthona euphoridae*, *Apion* spp., *Apogonia* spp., *Athous haemorrhoidalis*, *Atomaria* spp. such as *A. linearis*; *Attagenus* spp., *Aulacophora femoralis*, *Blastophagus piniperda*, *Blitophaga undata*, *Bruchidius obtectus*, *Bruchus* spp. such as *B. lentis*, *B. pisorum*, *B. rufimanus*; *Byctiscus betulae*, *Callidiellum rufipenne*, *Callopistria floridensis*, *Callosobruchus chinensis*, *Cameraria ohridella*, *Cassida nebulosa*, *Cerotoma trifurcata*, *Cetonia aurata*, *Ceuthorhynchus* spp. such as *C. assimilis*, *C. napi*; *Chaetocnema tibialis*, *Cleonus mendicus*, *Conoderus* spp. such as *C. vespertinus*; *Conotrachelus nenuphar*, *Cosmopolites* spp., *Costelytra zealandica*, *Crioceris asparagi*, *Cryptolestes ferrugineus*, *Cryptorhynchus lapathi*, *Ctenicera* spp. such as *C. destructor*; *Curculio* spp., *Cylindrocopturus* spp., *Cyclocephala* spp., *Dactylispa balyi*, *Dectes texanus*, *Dermestes* spp., *Diabrotica* spp. such as *D. undecimpunctata*, *D. speciosa*, *D. longicornis*, *D. semipunctata*, *D. virgifera*; *Diaprepes abbreviates*, *Dichocrocis* spp., *Dicladispa armigera*, *Diloboderus abderus*, *Diocalandra frumenti* (*Diocalandra stigmaticollis*), *Enaphalodes rufulus*, *Epilachna* spp. such as *E. varivestis*, *E. vigintioctomaculata*; *Epitrix* spp. such as *E. hirtipennis*, *E. similaris*; *Eutheola humilis*, *Eutinobothrus brasiliensis*, *Faustinus cubae*, *Gibbium psylloides*, *Gnathocerus cornutus*, *Hellula undalis*, *Heteronychus arator*, *Hylamorpha elegans*, *Hylobius abietis*, *Hylotrupes bajulus*, *Hypera* spp. such as *H. brunneipennis*, *H. postica*; *Hypomeces squamosus*, *Hypothenemus* spp., *Ips typographus*, *Lachnosterna consanguinea*, *Lasioderma serricorne*, *Latheticus oryzae*, *Lathridius* spp., *Lema* spp. such as *L. bilineata*, *L. melanopus*; *Leptinotarsa* spp. such as *L. decemlineata*; *Leptispa pygmaea*, *Limonius californicus*, *Lissorhoptrus oryzophilus*, *Lixus* spp., *Luperodes* spp., *Lyctus* spp. such as *L. bruneus*; *Liogenys fuscus*, *Macrodactylus* spp. such as *M. subspinosus*; *Maladera matrida*, *Megaplatypus mutates*, *Megascelis* spp., *Melanotus communis*, *Meligethes* spp. such as *M. aeneus*; *Melolontha* spp. such as *M. hippocastani*, *M. melolontha*; *Metamasius hemipterus*, *Microtheca* spp., *Migdolus* spp. such as *M. fryanus*, *Monochamus* spp. such as *M. alternatus*; *Naupactus xanthographus*, *Niptus hololeucus*, *Oberia brevis*, *Oemona hirta*, *Oryctes rhinoceros*, *Oryzaephilus surinamensis*, *Oryzaphagus oryzae*, *Otiorrhynchus sulcatus*, *Otiorrhynchus ovatus*, *Otiorrhynchus sulcatus*, *Oulema melanopus*, *Oulema oryzae*, *Oxycetonia jucunda*, *Phaedon* spp. such as *P. brassicae*, *P. cochleariae*; *Phoracantha recurva*, *Phyllobius pyri*, *Phyllopertha horticola*, *Phyllophaga* spp. such as *P. helleri*; *Phyllotreta* spp. such as *P. chrysocephala*, *P. nemorum*, *P. striolata*, *P. vittula*; *Phyllopertha horticola*, *Popillia japonica*, *Premnotrypes* spp., *Psacothea hilaris*, *Psylliodes chrysocephala*, *Prostephanus truncates*, *Psylliodes* spp., *Ptinus* spp., *Pulga saltona*, *Rhizopertha dominica*, *Rhynchophorus* spp. such as *R. billineatus*, *R. ferrugineus*, *R. palmarum*, *R. phoenicis*, *R. vulneratus*; *Saperda Candida*, *Scolytus schevyrewi*, *Scyphophorus acupunctatus*, *Sitona lineatus*, *Sitophilus* spp. such as *S. granaria*, *S. oryzae*, *S. zeamais*; *Sphenophorus* spp. such as *S. levis*; *Stegobium paniceum*, *Sternechus* spp. such as *S. subsignatus*; *Strophomorphus ctenotus*, *Symphyletes* spp., *Tanymecus* spp., *Tenebrio molitor*, *Tenebrioides mauretanicus*, *Tribolium* spp. such as *T. castaneum*; *Trogoderma* spp., *Tychius* spp., *Xylotrechus* spp. such as *X. pyrrhoderus*; and, *Zabrus* spp. such as *Z. tenebrioides*; insects from the order of Diptera for example *Aedes* spp. such as *A. aegypti*, *A. albopictus*, *A. vexans*; *Anastrepha ludens*, *Anopheles* spp. such as *A. albimanus*, *A. crucians*, *A. freeborni*, *A. gambiae*, *A. leucosphyrus*, *A. maculipennis*, *A. minimus*, *A. quadrimaculatus*, *A. sinensis*; *Bactrocera invadens*, *Bibio hortulanus*, *Calliphora erythrocephala*, *Calliphora vicina*, *Ceratitis capitata*, *Chrysomyia* spp. such as *C. bezziana*, *C. hominivorax*, *C. macellaria*; *Chrysops atlanticus*, *Chrysops discalis*, *Chrysops silacea*, *Cochliomyia* spp. such as *C. hominivorax*; *Contarinia* spp. such as *C. sorghicola*; *Cordylobia anthropophaga*, *Culex* spp. such as *C. nigripalpus*, *C. pipiens*, *C. quinquefasciatus*, *C. tarsalis*, *C. tritaeniorhynchus*; *Culi-*

*coides furens, Culiseta inornata, Culiseta melanura, Cuterebra* spp., *Dacus cucurbitae, Dacus oleae, Dasineura brassicae, Dasineura oxycoccana, Delia* spp. such as *D. antique, D. coarctata, D. platura, D. radicum; Dermatobia hominis, Drosophila* spp. such as *D. suzukii, Fannia* spp. such as *F. canicularis; Gastraphilus* spp. such as *G. intestinalis; Geomyza tipunctata, Glossina* spp. such as *G. fuscipes, G. morsitans, G. palpalis, G. tachinoides; Haematobia irritans, Haplodiplosis equestris, Hippelates* spp., *Hylemyia* spp. such as *H. platura; Hypoderma* spp. such as *H. lineata; Hyppobosca* spp., *Hydrellia philippina, Leptoconops torrens, Liriomyza* spp. such as *L. sativae, L. trifolii; Lucilia* spp. such as *L. caprina, L. cuprina, L. sericata; Lycoria pectoralis, Mansonia titillanus, Mayetiola* spp. such as *M. destructor; Musca* spp. such as *M. autumnalis, M. domestica; Muscina stabulans, Oestrus* spp. such as *O. ovis; Opomyza florum, Oscinella* spp. such as *O. frit; Orseolia oryzae, Pegomya hysocyami, Phlebotomus argentipes, Phorbia* spp. such as *P. antiqua, P. brassicae, P. coarctata; Phytomyza gymnostoma, Prosimulium mixtum, Psila rosae, Psorophora columbiae, Psorophora discolor, Rhagoletis* spp. such as *R. cerasi, R. cingulate, R. indifferens, R. mendax, R. pomonella; Rivellia quadrifasciata, Sarcophaga* spp. such as *S. haemorrhoidalis; Simulium vittatum, Sitodiplosis mosellana, Stomoxys* spp. such as *S. calcitrans; Tabanus* spp. such as *T. atratus, T. bovinus, T. lineola, T. similis; Tannia* spp., *Thecodiplosis japonensis, Tipula oleracea, Tipula paludosa*, and *Wohlfahrtia* spp; insects from the order of Thysanoptera for example, *Baliothrips biformis, Dichromothrips corbetti, Dichromothrips* ssp., *Echinothrips americanus, Enneothrips flavens, Frankliniella* spp. such as *F. fusca, F. occidentalis, F. tritici; Heliothrips* spp., *Hercinothrips femoralis, Kakothrips* spp., *Microcephalothrips abdominalis, Neohydatothrips samayunkur, Pezothrips kellyanus, Rhipiphorothrips cruentatus, Scirtothrips* spp. such as *S. citri, S. dorsalis, S. perseae; Stenchaetothrips* spp, *Taeniothrips cardamoni, Taeniothrips inconsequens, Thrips* spp. such as *T. imagines, T. hawaiiensis, T. oryzae, T. palmi, T. parvispinus, T. tabaci*; insects from the order of Hemiptera for example, *Acizzia jamatonica, Acrosternum* spp. such as *A. hilare; Acyrthosipon* spp. such as *A. onobrychis, A. pisum; Adelges laricis, Adelges tsugae, Adelphocoris* spp., such as *A. rapidus, A. superbus; Aeneolamia* spp., *Agonoscena* spp., *Aulacorthum solani, Aleurocanthus woglumi, Aleurodes* spp., *Aleurodicus disperses, Aleurolobus barodensis, Aleurothrixus* spp., *Amrasca* spp., *Anasa tristis, Antestiopsis* spp., *Anuraphis cardui, Aonidiella* spp., *Aphanostigma piri, Aphidula nasturtii, Aphis* spp. such as *A. craccivora, A. fabae, A. forbesi, A. gossypii, A. grossulariae, A. maidiradicis, A. pomi, A. sambuci, A. schneideri, A. spiraecola; Arboridia apicalis, Arilus critatus, Aspidiella* spp., *Aspidiotus* spp., *Atanus* spp., *Aulacaspis yasumatsui, Aulacorthum solani, Bactericera cockerelli (Paratrioza cockerelli), Bemisia* spp. such as *B. argentifolii, B. tabaci (Aleurodes tabaci); Blissus* spp. such as *B. leucopterus; Brachycaudus* spp. such as *B. cardui, B. helichrysi, B. persicae, B. prunicola; Brachycolus* spp., *Brachycorynella asparagi, Brevicoryne brassicae, Cacopsylla* spp. such as *C. fulguralis, C. pyricola (Psylla piri); Calligypona marginata, Calocoris* spp., *Campylomma livida, Capitophorus horni, Carneocephala fulgida, Cavelerius* spp., *Ceraplastes* spp., *Ceratovacuna lanigera, Ceroplastes ceriferus, Cerosipha gossypii, Chaetosiphon fragaefolii, Chionaspis tegalensis, Chlorita onukii, Chromaphis juglandicola, Chrysomphalus ficus, Cicadulina mbila, Cimex* spp. such as *C. hemipterus, C. lectularius; Coccomytilus halli, Coccus* spp. such as *C. hesperidum, C. pseudomagnoliarum, Corythucha arcuata, Creontiades dilutus, Cryptomyzus ribis, Chrysomphalus aonidum, Cryptomyzus ribis, Ctenarytaina spatulata, Cyrtopeltis notatus, Dalbulus* spp., *Dasynus piperis, Dialeurodes* spp. such as *D. citrifolii; Dalbulus maidis, Diaphorina* spp. such as *D. citri; Diaspis* spp. such as *D. bromeliae; Dichelops furcatus, Diconocoris hewetti, Doralis* spp., *Dreyfusia nordmannianae, Dreyfusia piceae, Drosicha* spp., *Dysaphis* spp. such as *D. plantaginea, D. pyri, D. radicola; Dysaulacorthum pseudosolani, Dysdercus* spp. such as *D. cingulatus, D. intermedius; Dysmicoccus* spp., *Edessa* spp., *Geocoris* spp., *Empoasca* spp. such as *E. fabae, E. solana; Epidiaspis leperii, Eriosoma* spp. such as *E. lanigerum, E. pyricola; Erythroneura* spp., *Eurygaster* spp. such as *E. integriceps; Euscelis bilobatus, Euschistus* spp. such as *E. heros, E. impictiventris, E. servus; Fiorinia theae, Geococcus coffeae, Glycaspis brimblecombei, Halyomorpha* spp. such as *H. halys; Heliopeltis* spp., *Homalodisca vitripennis (=H. coagulata), Horcias nobilellus, Hyalopterus pruni, Hyperomyzus lactucae, Icerya* spp. such as *I. purchase; Idiocerus* spp., *Idioscopus* spp., *Laodelphax striatellus, Lecanium* spp., *Lecanoideus floccissimus, Lepidosaphes* spp. such as *L. ulmi; Leptocorisa* spp., *Leptoglossus phyllopus, Lipaphis erysimi, Lygus* spp. such as *L. hesperus, L. lineolaris, L. pratensis; Maconellicoccus hirsutus, Marchalina hellenica, Macropes excavatus, Macrosiphum* spp. such as *M. rosae, M. a venae, M. euphorbiae; Macrosteles quadrilineatus, Mahanarva fimbriolata, Megacopta cribraria, Megoura viciae, Melanaphis pyrarius, Melanaphis sacchari, Melanocallis (=Tinocallis) caryaefoliae, Metcafiella* spp., *Metopolophium dirhodum, Monellia costalis, Monelliopsis pecanis, Myzocallis coryli, Murgantia* spp., *Myzus* spp. such as *M. ascalonicus, M. cerasi, M. nicotianae, M. persicae, M. varians; Nasonovia ribis-nigri, Neotoxoptera formosana, Neomegalotomus* spp. *Nephotettix* spp. such as *N. malayanus, N. nigropictus, N. parvus, N. virescens; Nezara* spp. such as *N. viridula; Nilaparvata lugens, Nysius huttoni, Oebalus* spp. such as *O. pugnax; Oncometopia* spp., *Orthezia praelonga, Oxycaraenus hyalinipennis, Parabemisia myricae, Parlatoria* spp., *Parthenolecanium* spp. such as *P. corni, P. persicae; Pemphigus* spp. such as *P. bursarius, P. populivenae; Peregrinus maidis, Perkinsiella saccharicida, Phenacoccus* spp. such as *P. aceris, P. gossypii; Phloeomyzus passerinii, Phorodon humuli, Phylloxera* spp. such as *P. devastatrix, Piesma quadrata, Piezodorus* spp. such as *P. guildinii; Pinnaspis aspidistrae, Planococcus* spp. such as *P. citri, P. ficus; Prosapia bicincta, Protopulvinaria pyriformis, Psallus seriatus, Pseudacysta persea, Pseudaulacaspis pentagona, Pseudococcus* spp. such as *P. comstocki; Psylla* spp. such as *P. mali; Pteromalus* spp., *Pulvinaria amygdali, Pyrilla* spp., *Quadraspidiotus* spp., such as *Q. perniciosus; Quesada gigas, Rastrococcus* spp., *Reduvius senilis, Rhizoecus americanus, Rhodnius* spp., *Rhopalomyzus ascalonicus, Rhopalosiphum* spp. such as *R. pseudobrassicas, R. insertum, R. maidis, R. padi; Sagatodes* spp., *Sahlbergella singularis, Saissetia* spp., *Sappaphis mala, Sappaphis mali, Scaptocoris* spp., *Scaphoides titanus, Schizaphis graminum, Schizoneura lanuginosa, Scotinophora* spp., *Selenaspidus articulatus, Sitobion a venae, Sogata* spp., *Sogatella furcifera, Solubea insularis, Spississtilus festinus (=Stictocephala festina), Stephanitis nashi, Stephanitis pyrioides, Stephanitis takeyai, Tenalaphara malayensis, Tetraleurodes perseae, Therioaphis maculate, Thyanta* spp. such as *T. accerra, T. perditor; Tibraca* spp., *Tomaspis* spp., *Toxoptera* spp. such as *T. aurantii; Trialeurodes* spp. such as *T. abutilonea, T. ricini, T. vaporariorum; Triatoma* spp., *Trioza* spp., *Typhlocyba* spp., *Unaspis* spp. such as *U. citri, U. yanonensis;* and *Viteus vitifolii*, insects from the order Hymenoptera for example *Acanthomyops interjectus, Athalia rosae, Atta* spp. such as *A. capiguara, A. cephalotes, A. cephalotes, A. laevigata, A. robusta, A. sexdens, A. texana, Bombus* spp., *Brachymyrmex* spp., *Camponotus* spp. such as *C. floridanus, C. pennsylvanicus, C. modoc; Cardiocondyla nuda, Chalibion* sp, *Crematogaster* spp., *Dasymutilla occidentalis, Diprion* spp., *Dolichovespula maculata, Dorymyrmex* spp., *Dryocosmus kuriphilus, Formica* spp., *Hoplocampa* spp. such as *H. minuta, H. testudinea; Iridomyrmex humilis, Lasius* spp. such as *L. niger, Linepithema humile, Liometopum* spp., *Leptocybe invasa, Monomorium* spp. such as *M. pharaonis, Monomorium, Nylandria fulva, Pachycondyla chinensis, Paratrechina longicornis, Paravespula* spp., such as *P. germanica, P. pennsylvanica, P. vulgaris; Pheidole* spp. such as *P. megacephala; Pogonomyrmex* spp. such as *P. barbatus, P. californicus, Polistes rubiginosa, Prenolepis impairs, Pseudomyrmex gracilis, Schelipron* spp., *Sirex cyaneus, Solenopsis* spp. such as *S. geminata, S. invicta, S. molesta, S. richteri, S. xyloni, Sphecius speciosus, Sphex* spp., *Tapinoma* spp. such as *T. melanocephalum, T. sessile; Tetramorium* spp. such as *T. caespitum, T. bicarinatum, Vespa* spp. such as *V. crabro; Vespula* spp. such as *V. squamosal; Wasmannia auropunctata, Xylocopa* sp; insects from the order Orthoptera for example *Acheta domesticus, Calliptamus italicus, Chortoicetes terminifera, Ceuthophilus* spp., *Diastrammena asynamora, Dociostaurus maroccanus, Gryllotalpa* spp. such as *G. africana, G. gryllotalpa; Gryllus* spp., *Hieroglyphus daganensis, Kraussaria angulifera, Locusta* spp. such *as L. migratoria, L. pardalina; Melanoplus* spp. such as *M. bivittatus, M. femurrubrum, M. mexicanus, M. sanguinipes, M. spretus; Nomadacris septemfasciata, Oedaleus senegalensis, Scapteriscus* spp., *Schistocerca* spp. such as *S. americana, S. gregaria, Stemopelmatus* spp., *Tachycines asynamorus,* and *Zonozerus variegatus*; pests from the Class Arachnida for example Acari, e.g. of the families Argasidae, Ixodidae and Sarcoptidae, such as *Amblyomma* spp. (e.g. *A. americanum, A. variegatum, A. maculatum*), *Argas* spp. such as *A. persicu*), *Boophilus* spp. such *as B. annulatus, B. decoloratus, B. microplus, Dermacentor* spp. such as *D. silvarum, D. andersoni, D. variabilis, Hyalomma* spp. such as *H. truncatum, Ixodes* spp. such as *I. ricinus, I. rubicundus, I. scapularis, I. holocyclus, I. pacificus, Rhipicephalus sanguineus, Ornithodorus* spp. such as *O. moubata, O. hermsi, O. turicata, Ornithonyssus bacoti, Otobius megnini, Dermanyssus gallinae, Psoroptes* spp. such as *P. ovis, Rhipicephalus* spp. such as *R. sanguineus, R. appendiculatus, Rhipicephalus evertsi, Rhizoglyphus* spp., *Sarcoptes* spp. such as *S. Scabiei,* and Family Eriophyidae including *Aceria* spp. such as *A. sheldoni, A. anthocoptes, Acallitus* spp., *Aculops* spp. such as *A. lycopersici, A. pelekassi, Aculus* spp. such as *A. schlechtendali; Colomerus vitis, Epitrimerus pyri, Phyllocoptruta oleivora; Eriophytes ribis* and *Eriophyes* spp. such as *Eriophyes sheldoni*, Family Tarsonemidae including *Hemitarsonemus* spp., *Phytonemus pallidus* and *Polyphagotarsonemus latus, Stenotarsonemus* spp. *Steneotarsonemus spinki*, Family Tenuipalpidae including *Brevipalpus* spp. such as *B. phoenicis*, Family Tetranychidae including *Eotetranychus* spp., *Eutetranychus* spp., *Oligonychus* spp., *Petrobia latens, Tetranychus* spp. such as *T. cinnabarinus, T. evansi, T. kanzawai, T. pacificus, T. phaseulus, T. telarius* and *T. urticae, Bryobia praetiosa; Panonychus* spp. such as *P. ulmi, P. citri, Metatetranychus* spp. and *Oligonychus* spp. such as *O. pratensis, O. perseae, Vasates lycopersici, Raoiella indica,* Family Carpoglyphidae including *Carpoglyphus* spp.; *Penthaleidae* spp. such as *Halotydeus destructor,* Family Demodicidae with species such as *Demodex* spp.; Family Trombicidea including *Trombicula* spp.; Family Macronyssidae including *Ornothonyssus* spp.; Family Pyemotidae including *Pyemotes tritici, Tyrophagus putrescentiae,* Family Acaridae including *Acarus siro,* Family Araneida including *Latrodectus mactans, Tegenaria agrestis, Chiracanthium* sp, *Lycosa* sp *Achaearanea tepidariorum* and *Loxosceles reclusa,* pests from the Phylum Nematoda, for example, plant parasitic nematodes such as root-knot nematodes, *Meloidogyne* spp. such as *M. hapla, M. incognita, M. javanica;* cyst-forming nematodes, *Globodera* spp. such as *G. rostochiensis; Heterodera* spp. such as *H. avenae, H. glycines, H. schachtii, H. trifolii*; Seed gall nematodes, *Anguina* spp.; Stem and foliar nematodes, *Aphelenchoides* spp. such as *A. besseyi;* Sting nematodes, *Belonolaimus* spp. such as *B. longicaudatus;* Pine nematodes, *Bursaphelenchus* spp. such as *B. lignicolus, B. xylophilus;* Ring nematodes, *Criconema* spp., *Criconemella* spp. such as *C. xenoplax* and *C. ornata;* and, *Criconemoides* spp. such as *Criconemoides informis; Mesocriconema* spp.; Stem and bulb nematodes, *Ditylenchus* spp. such as *D. destructor, D. dipsaci;* Awl nematodes, *Dolichodorus* spp.; Spiral nematodes, *Heliocotylenchus multicinctus;* Sheath and sheathoid nematodes, *Hemicycliophora* spp. and *Hemicriconemoides* spp.; *Hirshmanniella* spp.; Lance nematodes, *Hoploaimus* spp.; False rootknot nematodes, *Nacobbus* spp.; Needle nematodes, *Longidorus* spp. such as *L. elongatus;* Lesion nematodes, *Pratylenchus* spp. such as *P. brachyurus, P. neglectus, P. penetrans, P. curvitatus, P. goodeyi;* Burrowing nematodes, *Radopholus* spp. such as *R. similis; Rhadopholus* spp.; *Rhodopholus* spp.; Reniform nematodes, *Rotylenchus* spp. such as *R. robustus, R. reniformis; Scutellonema* spp.; Stubby-root nematode, *Trichodorus* spp. such as *T. obtusus, T. primitivus; Paratrichodorus* spp. such as *P. minor;* Stunt nematodes, *Tylenchorhynchus* spp. such as *T. claytoni, T. dubius;* Citrus nematodes, *Tylenchulus* spp. such as *T. semipenetrans;* Dagger nematodes, *Xiphinema* spp.; and other plant parasitic nematode species; insects from the order Isoptera for example *Calotermes flavicollis, Coptotermes* spp. such as *C. formosanus, C. gestroi, C. acinaciformis; Cornitermes cumulans, Cryptotermes* spp. such as *C. brevis, C. cavifrons; Globitermes sulfureus, Heterotermes* spp. such as *H. aureus, H. longiceps, H. tenuis; Leucotermes flavipes, Odontotermes* spp., *Incisitermes* spp. such as *I. minor, I. Snyder, Marginitermes hubbardi, Mastotermes* spp. such as *M. darwiniensis Neocapritermes* spp. such as *N. opacus, N. parvus; Neotermes* spp., *Procornitermes* spp., *Zootermopsis* spp. such as *Z. angusticollis, Z. nevadensis, Reticulitermes* spp. such as *R. hesperus, R. tibialis, R. speratus, R. flavipes, R. grassei, R. lucifugus, R. santonensis, R. virginicus; Termes natalensis;* insects from the order Blattaria for example *Blatta* spp. such as *B. orientalis, B. lateralis; Blattella* spp. such as *B. asahinae, B. germanica; Leucophaea maderae, Panchlora nivea, Periplaneta* spp. such as *P. americana, P. australasiae, P. brunnea, P. fuligginosa, P. japonica; Supella longipalpa, Parcoblatta pennsylvanica, Eurycotis floridana, Pycnoscelus surinamensis,* insects from the order Siphonoptera for example *Cediopsylla simples, Ceratophyllus* spp., *Ctenocephalides* spp. such as *C. felis, C. canis, Xenopsylla cheopis, Pulex irritans, Trichodectes canis, Tunga penetrans,* and *Nosopsyllus fasciatus,*

Insects from the order Thysanura for example *Lepisma saccharina, Ctenoleplsma urbana,* and *Thermobia domestica,* pests from the class Chilopoda for example *Geophilus* spp., *Scutigera* spp. such as *Scutigera coleoptrata,* pests from the class Diplopoda for example *Blaniulus guttulatus, Julus* spp., *Narceus* spp.; pests from the class Symphyla for example *Scutigerella immaculata*; insects from the order Dermaptera, for example *Forficula auricularia*; insects from the order Collembola, for example *Onychiurus* spp., such as *Onychiurus armatus*; pests from the order Isopoda for example, *Armadillidium vulgare, Oniscus asellus, Porcellio scaber*, Insects from the order Phthiraptera, for example *Damalinia* spp., *Pediculus* spp. such as *Pediculus humanus capitis, Pediculus humanus corporis, Pediculus humanus humanus; Pthirus pubis, Haematopinus* spp. such as *Haematopinus eurysternus, Haematopinus suis, Linognathus* spp. such as *Linognathus vituli; Bovicola bovis, Menopon gallinae, Menacanthus stramineus* and *Solenopotes capillatus, Trichodectes* spp. Examples of further pest species which may be controlled by compounds of formula (I) include: from the Phylum Mollusca, class Bivalvia, for example, *Dreissena* spp.; class Gastropoda, for example, *Arion* spp., *Biomphalaria* spp., *Bulinus* spp., *Deroceras* spp., *Galba* spp., *Lymnaea* spp., *Oncomelania* spp., *Pomacea canaliclata, Succinea* spp.; from the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp. such as *Haemonchus contortus; Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercora lis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti*

In one embodiment, the methods and uses of the application relate to plants that carry a specific trait. The term "trait" relates to a specific feature, or a combination of features of a plant that has been added either by conventional breeding, i.e. a plant, which has not been modified by mutagenesis, or genetic engineering, or to features of a plant that have been added by mutagenesis, or genetic engineering. This feature, or the combination of features, are described in comparison to the respective non-modified control plants, i.e. plants that were not subjected to procedures for producing a plant that carries the same trait. The term "trait" in its singular, as used in this application, also refers to combinations of traits. Such traits may enable a maize plant to be resistant to active ingredients, such as herbicides, or to produce biologically active compounds that control infestation by plant pests. Examples of traits are better plant growth, increased tolerance to high or low temperatures, increased tolerance to drought, or to water or soil salt content, increased flowering performance, easier harvesting, accelerated maturation, higher harvest yields, higher quality and/or a higher nutritional value of the harvested products, better storage stability and/or processability of the harvested products.

Thus, for example, reduced application rates and/or a widening of the activity spectrum and/or an increase in the activity of the substances and compositions which can be used according to the invention, better plant growth, increased tolerance to high, or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected. Further and particularly emphasized examples of such traits are a better defense of the plants against animal and microbial pests, such as against insects, mites, phytopathogenic fungi, bacteria and/or viruses, and also increased tolerance of the plants to certain herbicidal active compounds. Preferred traits are insect resistance, more preferably resistance against Coleopterans, Hemipterans, and Lepidopterans, most preferably resistance against Coleopterans. Usually, the disclosed methods and uses relate to maize plants, which are commercially available. Depending on the maize plant and its traits, its location and growth conditions (soils, climate, vegetation period, diet), the uses and methods of application according to the invention may also result in superadditive ("synergistic") effects. Examples of genetically modified maize plants, as well of traits, and modified and/or incorporated genes are listed in Table B. Single rows and combinations of rows are each embodiments of maize plants for the disclosed uses and methods of application. Maize plants that were assigned with a specific tradename are commercially available. All other can be produced by the skilled person based on the Event Code by known methods, or can be obtained from deposition facilities of biological material.

TABLE B

Events, traits, genes, and developing companies of *Zea mays* plants and/or propagation material. Explanations for abbreviations are listed in Table C.

| No | Event Name | Event Code | Tradename | Trait (Trait type)/Gene | Developing/Producing Company |
|---|---|---|---|---|---|
| 1 | 32138 | DP-32138-1 | 32138 SPT maintainer | PC (FR)/ms45<br>PC (MS)/zm-aa1 | DuPont |
| 2 | 3272 | SYN-E3272-5 | Enogen ™ | ST (CA)/amy797E | Syngenta |
| 3 | 3272 × Bt11 | SYN-E3272-5 × SYN-BTØ11-1 | | ST (CA)/amy797E<br>IR (BL)/cry1Ab<br>HT (Glu)/pat | Syngenta |
| 4 | 3272 × Bt11 × GA21 | SYN-E3272-5 × SYN-BTØ11-1 × MON-ØØØ21-9 | | ST (CA)/amy797E<br>IR (BL)/cry1Ab<br>HT (Glu)/pat<br>HT (Gly)/mepsps | Syngenta |
| 5 | 3272 × Bt11 × MIR604 | SYN-E3272-5 × SYN-BTØ11-1 × SYN-IR6Ø4-5 | | ST (CA)/amy797E<br>IR (BL)/cry1Ab<br>HT (Glu)/pat<br>IR (Col)/mcry3A | Syngenta |

TABLE B-continued

Events, traits, genes, and developing companies of Zea mays plants and/or propagation material. Explanations for abbreviations are listed in Table C.

| No | Event Name | Event Code | Tradename | Trait (Trait type)/Gene | Developing/Producing Company |
|---|---|---|---|---|---|
| 6 | 3272 × MIR604 × GA21 | SYN-E3272-5 × SYN-BTØ11-1 × SYN-IRØ4-5 × MON-ØØØ21-9 | Enogen/Agrisure 3000GT | ST (CA)/amy797E<br>IR (BL)/cry1Ab<br>HT (Glu)/pat<br>IR (Col)/mcry3A<br>HT (Gly)/mepsps | Syngenta |
| 7 | 3272 × GA21 | SYN-E3272-5 × MON-ØØØ21-9 | | ST (CA)/amy797E<br>HT (Gly)/mepsps | Syngenta |
| 8 | 3272 × MIR604 | SYN-E3272-5 × SYN-IRØ4-5 | | ST (CA)/amy797E<br>IR (Col)/mcry3A | Syngenta |
| 9 | 3272 × MIR604 × GA21 | SYN-E3272-5 × SYN-IRØ4-5 × MON-ØØØ21-9 | | ST (CA)/amy797E<br>IR (Col)/mcry3A<br>HT (Gly)/mepsps | Syngenta |
| 10 | 33121 | DP-Ø33121-3 | | IR (BL)/cry2Ae<br>IR (BL)/cry1A<br>IR (BL)/vip3Aa20<br>HT (Glu)/pat | Dupont |
| 11 | 4114 | DP-ØØ4114-3 | | IR (BL)/cry1F<br>IR (Col)/cry34Ab1<br>IR (Col)/cry35Ab1<br>HT (Glu)/pat | Dupont |
| 12 | 5307 | SYN-Ø53Ø7-1 | Agrisure ® Duracade ™ | IR (Col)/ecry3.1Ab | Syngenta |
| 13 | 5307 × MIR604 × Bt11 × TC1507 × GA21 | SYN-Ø53Ø7-1 × SYN-IRØ4-5 × SYN-BTØ11-1 × DAS-Ø15Ø7-1 × MON-ØØØ21-9 | Agrisure ® Duracade ™ 5122 | IR (Col)/ecry3.1Ab<br>IR (Col)/mcry3A<br>IR (BL)/cry1Ab<br>HT (Glu)/pat<br>IR (BL)/cry1Fa2<br>HT (Gly)/mepsps | Syngenta |
| 14 | 5307 × MIR604 × Bt11 × TC1507 × GA21 × MIR162 | SYN-Ø53Ø7-1 × SYN-IRØ4-5 × SYN-BTØ11-1 × DAS-Ø15Ø7-1 × MON-ØØØ21-9 × SYN-IR162-4 | Agrisure ® Duracade ™ 5222 | IR (Col)/ecry3.1Ab<br>IR (Col)/mcry3A<br>IR (BL)/cry1Ab<br>HT (Glu)/pat<br>IR (BL)/cry1Fa2<br>HT (Gly)/mepsps<br>IR (BL)/vip3Aa20 | Syngenta |
| 15 | 59122 | DAS-59122-7 | Herculex ™ RW | HT (Glu)/pat<br>IR (Col)/cry34Ab1<br>IR (Col)/cry35Ab1 | Dow |
| 16 | 59122 × GA21 | DAS-59122-7 × MON-ØØØ21-9 | | HT (Glu)/pat<br>IR (Col)/cry34Ab1<br>IR (Col)/cry35Ab1<br>HT (Gly)/mepsps | Syngenta |
| 17 | 59122 × MIR604 | DAS-59122-7 × SYN-IRØ4-5 | | HT (Glu)/pat<br>IR (Col)/cry34Ab1<br>IR (Col)/cry35Ab1<br>IR (Col)/mcry3A | Syngenta |
| 18 | 59122 × MIR604 × GA21 | DAS-59122-7 × SYN-IRØ4-5 × MON-ØØØ21-9 | | HT (Glu)/pat<br>IR (Col)/cry34Ab1<br>IR (Col)/cry35Ab1<br>IR (Col)/mcry3A<br>HT (Gly)/mepsps | Syngenta |
| 19 | 59122 × MIR604 × TC1507 | DAS-59122-7 × SYN-IRØ4-5 × DAS-Ø15Ø7-1 | | HT (Glu)/pat<br>IR (Col)/cry34Ab1<br>IR (Col)/cry35Ab1<br>IR (Col)/mcry3A<br>IR (BL)/cry1Fa2 | Syngenta |
| 20 | 59122 × MIR604 × TC1507 × GA21 | DAS-59122-7 × SYN-IRØ4-5 × DAS-Ø15Ø7-1 × MON-ØØØ21-9 | | HT (Glu)/pat<br>IR (Col)/cry34Ab1<br>IR (Col)/cry35Ab1<br>IR (Col)/mcry3A<br>IR (BL)/cry1Fa2<br>HT (Gly)/mepsps | Syngenta |
| 21 | 59122 × MON810 | DAS-59122-7 × MON-ØØ81Ø-6 | | HT (Glu)/pat<br>IR (Col)/cry34Ab1<br>IR (Col)/cry35Ab1<br>IR (BL)/cry1Ab | Dupont |
| 22 | 59122 × MON810 × NK603 | DAS-59122-7 × MON-ØØ81Ø-6 × MON-ØØ6Ø3-6 | | HT (Glu)/pat<br>IR (Col)/cry34Ab1<br>IR (Col)/cry35Ab1<br>IR (BL)/cry1Ab<br>HT (Gly)/cp4 epsps (aroA:CP4) | Dupont |

TABLE B-continued

Events, traits, genes, and developing companies of *Zea mays* plants and/or propagation material. Explanations for abbreviations are listed in Table C.

| No | Event Name | Event Code | Tradename | Trait (Trait type)/ Gene | Developing/ Producing Company |
|---|---|---|---|---|---|
| 23 | 59122 × MON88017 | DAS-59122-7 × MON-88Ø17-3 | | HT (Glu)/pat<br>IR (Col)/cry34Ab1<br>IR (Col)/cry35Ab1<br>IR (Col)/cry3Bb1<br>HT (Gly)/cp4 epsps (aroA:CP4) | Monsanto & Dow |
| 24 | 59122 × NK603 | AS-59122-7 × MON-ØØ6Ø3-6 | Herculex ™ RW Roundup Ready ™ 2 | HT (Glu)/pat<br>IR (Col)/cry34Ab1<br>IR (Col)/cry35Ab1<br>HT (Gly)/cp4 epsps (aroA:CP4) | Dupont |
| 25 | 59122 × TC1507 × GA21 | DAS-59122-7 × DAS-Ø15Ø7-1 × MON-ØØØ21-9 | | HT (Glu)/pat<br>IR (Col)/cry34Ab1<br>IR (Col)/cry35Ab1<br>IR (BL)/cry1Fa2<br>HT (Gly)/mepsps | Syngenta |
| 26 | 676 | PH-ØØØ676-7 | | HT (Glu)/pat<br>PC (MS)/dam | Dupont |
| 27 | 678 | PH-ØØØ678-9 | | HT (Glu)/pat<br>PC (MS)/dam | Dupont |
| 28 | 680 | PH-ØØØ68Ø-2 | | HT (Glu)/pat<br>PC (MS)/dam | Dupont |
| 29 | 98140 | DP-Ø9814Ø-6 | Optimum ™ GAT ™ | HT (SU)/zm-hra<br>HT (Gly)/gat4621 | Dupont |
| 30 | 98140 × 59122 | DP-Ø9814Ø-6 × DAS-59122-7 | | HT (Glu)/pat<br>IR (Col)/cry34Ab1<br>IR (Col)/cry35Ab1<br>HT (SU)/zm-hra<br>HT (Gly)/gat4621 | Dow & Dupont |
| 31 | 98140 × TC1507 | DP-Ø9814Ø-6 × DAS-Ø15Ø7-1 | | HT (SU)/zm-hra<br>HT (Gly)/gat4621<br>IR (BL)/cry1Fa2<br>HT (Glu)/pat | Dow & Dupont |
| 32 | 98140 × TC1507 × 59122 | DP-Ø9814Ø-6 × DAS-Ø15Ø7-1 × DAS-59122-7 | | HT (Glu)/pat<br>IR (Col)/cry34Ab1<br>IR (Col)/cry35Ab1<br>HT (SU)/zm-hra<br>HT (Gly)/gat4621<br>IR (BL)/cry1Fa2 | Dow & Dupont |
| 33 | Bt10 | | Bt10 | IR (BL)/cry1Ab<br>HT (Glu)/pat | Syngenta |
| 34 | Bt11 (X4334CBR, X4734CBR) | SYN-BTØ11-1 | Agrisure ™ CB/LL | IR (BL)/cry1Ab<br>HT (Glu)/pat | Syngenta |
| 35 | Bt11 × 59122 | SYN-BTØ11-1 × DAS-59122-7 | | HT (Glu)/pat<br>IR (Col)/cry34Ab1<br>IR (Col)/cry35Ab1<br>IR (BL)/cry1Ab | Syngenta |
| 36 | Bt11 × 59122 × GA21 | SYN-BTØ11-1 × DAS-59122-7 × MON-ØØØ21-9 | | HT (Glu)/pat<br>IR (Col)/cry34Ab1<br>IR (Col)/cry35Ab1<br>IR (BL)/cry1Ab<br>HT (Gly)/mepsps | Syngenta |
| A37 | Bt11 × 59122 × MIR604 | SYN-BTØ11-1 × DAS-59122-7 × SYN-IR6Ø4-5 | | HT (Glu)/pat<br>IR (Col)/cry34Ab1<br>IR (Col)/cry35Ab1<br>IR (BL)/cry1Ab<br>IR (Col)/mcry3a | Syngenta |
| 38 | Bt11 × 59122 × MIR604 × GA21 | SYN-BTØ11-1 × DAS-59122-7 × SYN-IR6Ø4-5 × MON-ØØØ21-9 | | HT (Glu)/pat<br>IR (Col)/cry34Ab1<br>IR (Col)/cry35Ab1<br>IR (BL)/cry1Ab<br>IR (Col)/mcry3a<br>HT (Gly)/mepsps | Syngenta |
| 39 | Bt11 × 59122 × MIR604 × TC1507 | SYN-BTØ11-1 × DAS-59122-7 × SYN-IR6Ø4-5 × DAS-Ø15Ø7-1 | | HT (Glu)/pat<br>IR (Col)/cry34Ab1<br>IR (Col)/cry35Ab1<br>IR (BL)/cry1Ab<br>IR (BL)/cry1Fa2<br>IR (Col)/mcry3a | Syngenta |

TABLE B-continued

Events, traits, genes, and developing companies of Zea mays plants and/or propagation material. Explanations for abbreviations are listed in Table C.

| No | Event Name | Event Code | Tradename | Trait (Trait type)/Gene | Developing/Producing Company |
|---|---|---|---|---|---|
| 40 | BT11 × 59122 × MIR604 × TC1507 × GA21 | SYN-BTØ11-1 × DAS-59122-7 × SYN-IR6Ø4-5 × DAS-Ø15Ø7-1 × MON-ØØØ21-9 | Agrisure ® 3122 | HT (Glu)/pat<br>IR (Col)/cry34Ab1<br>IR (Col)/cry35Ab1<br>IR (BL)/cry1Ab<br>IR (BL)/cry1Fa2<br>IR (Col)/mcry3a<br>HT (Gly)/mepsps | Syngenta |
| 41 | Bt11 × 59122 × TC1507 | SYN-BTØ11-1 × DAS-59122-7 × DAS-Ø15Ø7-1 | | HT (Glu)/pat<br>IR (Col)/cry34Ab1<br>IR (Col)/cry35Ab1<br>IR (BL)/cry1Ab<br>IR (BL)/cry1Fa2 | Syngenta |
| 42 | Bt11 × 59122 × TC1507 × GA21 | SYN-BTØ11-1 × DAS-59122-7 × DAS-Ø15Ø7-1 × MON-ØØØ21-9 | | HT (Glu)/pat<br>IR (Col)/cry34Ab1<br>IR (Col)/cry35Ab1<br>IR (BL)/cry1Ab<br>IR (BL)/cry1Fa2<br>HT (Gly)/mepsps | Syngenta |
| 43 | Bt11 × GA21 | SYN-BTØ11-1 × MON-ØØØ21-9 | Agrisure ™ GT/CB/LL | HT (Gly)/mepsps<br>IR (BL)/cry1Ab<br>HT (Glu)/pat | Syngenta |
| 44 | Bt11 × MIR162 | SYN-BTØ11-1 × SYN-IR162-4 | Agrisure ® Viptera ™ 2100 | IR (BL)/cry1Ab (truncated)<br>HT (Glu)/pat<br>IR (BL)/vip3Aa20 | Syngenta |
| 45 | Bt11 × MIR162 × GA21 | SYN-BTØ11-1 × SYN-IR162-4 × MON-ØØØ21-9 | Agrisure ® Viptera ™ 3110 | IR (BL)/cry1Ab<br>HT (Glu)/pat<br>IR (BL)/vip3Aa20<br>HT (Gly)/mepsps | Syngenta |
| 46 | BT11 × MIR162 × MIR604 | SYN-BTØ11-1 × SYN-IR162-4 × SYN-IR6Ø4-5 | Agrisure ® Viptera ™ 3100 | IR (BL)/cry1Ab<br>HT (Glu)/pat<br>IR (BL)/vip3Aa20<br>IR (Col)/mcry3a | Syngenta |
| 47 | Bt11 × MIR162 × MIR604 × GA21 | SYN-BTØ11-1 × SYN-IR162-4 × SYN-IR6Ø4-5 × MON-ØØØ21-9 | Agrisure ® Viptera ™ 3111, Agrisure ® Viptera ™ 4 | IR (BL)/cry1Ab<br>HT (Glu)/pat<br>IR (BL)/vip3Aa20<br>IR (Col)/mcry3a<br>HT (Gly)/mepsps | Syngenta |
| 48 | Bt11 × MIR162 × TC1507 | SYN-BTØ11-1 × SYN-IR162-4 × DAS-Ø15Ø7-1 | | IR (BL)/cry1Ab<br>HT (Glu)/pat<br>IR (BL)/vip3Aa20<br>IR (BL)/cry1Fa2 | Syngenta |
| 49 | Bt11 × MIR162 × TC1507 × GA21 | SYN-BTØ11-1 × SYN-IR162-4 × DAS-Ø15Ø7-1 × MON-ØØØ21-9 | Agrisure ™ Viptera 3220 | IR (BL)/cry1Ab<br>HT (Glu)/pat<br>IR (BL)/vip3Aa20<br>IR (BL)/cry1Fa2<br>HT (Gly)/mepsps | Syngenta |
| 50 | Bt11 × MIR604 | SYN-BTØ11-1 × SYN-IR6Ø4-5 | Agrisure ™ CB/LL/RW | IR (BL)/cry1Ab<br>HT (Glu)/pat<br>IR (Col)/mcry3a | Syngenta |
| 51 | BT11 × MIR604 × GA21 | SYN-BTØ11-1 × SYN-IR6Ø4-5 × MON-ØØØ21-9 | Agrisure ™ 3000GT | IR (BL)/cry1Ab<br>HT (Glu)/pat<br>IR (Col)/mcry3a<br>HT (Gly)/mepsps | Syngenta |
| 52 | Bt11 × MIR604 × TC1507 | SYN-BTØ11-1 × SYN-IR6Ø4-5 × DAS-Ø15Ø7-1 | | IR (BL)/cry1Ab<br>HT (Glu)/pat<br>IR (Col)/mcry3a<br>IR (BL)/cry1Fa2 | Syngenta |
| 53 | Bt11 × TC1507 | SYN-BTØ11-1 × DAS-Ø15Ø7-1 | | IR (BL)/cry1Ab<br>HT (Glu)/pat<br>IR (BL)/cry1Fa2 | Syngenta |
| 54 | Bt11 × TC1507 × GA21 | SYN-BTØ11-1 × DAS-Ø15Ø7-1 × MON-ØØØ21-9 | | IR (BL)/cry1Ab<br>HT (Glu)/pat<br>IR (BL)/cry1Fa2<br>HT (Gly)/mepsps | Syngenta |
| 55 | Bt176 (176) | SYN-EV176-9 | NaturGard KnockOut ™, Maximizer ™ | IR (BL)/cry1Ab<br>HT (Glu)/bar | Syngenta |
| 56 | BVLA430101 | | | ST (P)/phyA2 | Origin Agritech (China) |
| 57 | CBH-351 | ACS-ZMØØ4-3 | Starlink ™ Maize | IR (BL)/cry9c<br>HT (Glu)/bar | Bayer Crop Sciences |
| 58 | DAS40278 | DAS-4Ø278-9 | Enlist ™ Maize | HT (2,4-D)/aad1 | Dow |

TABLE B-continued

Events, traits, genes, and developing companies of Zea mays plants and/or propagation material. Explanations for abbreviations are listed in Table C.

| No | Event Name | Event Code | Tradename | Trait (Trait type)/Gene | Developing/Producing Company |
|---|---|---|---|---|---|
| 59 | DAS40278 × NK603 | DAS-4Ø278-9 × MON-ØØ6Ø3-6 | Roundup Ready Corn 2 Enlist ™ | HT (2,4-D)/aad1<br>HT (Gly)/cp4 epsps (aroA:CP4) | Dow |
| 60 | DBT418 | DKB-89614-9 | Bt Xtra ™ Maize | IR (BL)/Cry1Ac<br>IR (BL)/pin2<br>HT (Glu)/bar | Monsanto |
| 61 | DLL25 (B16) | DKB-8979Ø-5 | | HT (Glu)/bar | Monsanto |
| 62 | GA21 | MON-ØØØ21-9 | Roundup Ready ™ Maize, Agrisure ™GT | HT (Gly)/mepsps | Monsanto |
| 63 | GA21 × MON810 | MON-ØØØ21-9 × MON-ØØ81Ø-6 | Roundup Ready ™ Yield-Gard ™maize | IR (BL)/cry1Ab<br>HT (Gly)/mepsps | Monsanto |
| 64 | GA21 × T25 | MON-ØØØ21-9 × ACS-ZMØØ3-2 | | HT (Gly)/mepsps<br>HT (Glu)/pat (syn) | Syngenta |
| 65 | HCEM485 | HCEM485 | | HT (Gly)/2mepsps | Stine Seed Farm, Inc (USA) |
| 66 | LY038 | REN-ØØØ38-3 | Mavera ™ Maize | ST (AA)/cordapA | Renessen LLC (Netherlands) |
| 67 | LY038 × MON810 | REN-ØØØ38-3 × MON-ØØ81Ø-6 | Mavera ™ Yield Gard ™Maize | ST (AA)/cordapA<br>IR (BL)/cry1Ab | Renessen LLC (Netherlands) & Monsanto |
| 68 | MIR162 | SYN-IR162-4 | Agrisure ™ Viptera | IR (BL)/vip3Aa20 | Syngenta |
| 69 | MIR162 × GA21 | SYN-IR162-4 × MON-ØØØ21-9 | | IR (BL)/vip3Aa20<br>HT (Gly)/mepsps | Syngenta |
| 70 | MIR162 × MIR604 | SYN-IR162-4 × SYN-IR6Ø4-5 | | IR (BL)/vip3Aa20<br>IR (Col)/mcry3a | Syngenta |
| 71 | MIR162 × MIR604 × GA21 | SYN-IR162-4 × SYN-IR6Ø4-5 × MON-ØØØ21-9 | | IR (BL)/vip3Aa20<br>IR (Col)/mcry3a<br>HT (Gly)/mepsps | Syngenta |
| 72 | MIR162 × TC1507 | SYN-IR162-4 × DAS-Ø15Ø7-1 | | IR (BL)/vip3Aa20<br>IR (BL)/cry1Fa2<br>HT (Glu)/pat | Syngenta |
| 73 | MIR162 × TC1507 × GA21 | SYN-IR162-4 × DAS-Ø15Ø7-1 × MON-ØØØ21-9 | | IR (BL)/vip3Aa20<br>IR (BL)/cry1Fa2<br>HT (Glu)/pat<br>HT (Gly)/mepsps | Syngenta |
| 74 | MIR604 | SYN-IR6Ø4-5 | Agrisure ™ RW | IR (Col)/mcry3a | Syngenta |
| 75 | MIR604 × GA21 | SYN-IR6Ø4-5 × MON-ØØØ21-9 | Agrisure ™ GT/RW | IR (Col)/mcry3a<br>HT (Gly)/mepsps | Syngenta |
| 76 | MIR604 × NK603 | SYN-IR6Ø4-5 × MON-ØØ6Ø3-6 | | IR (Col)/mcry3a<br>HT (Gly)/cp4 epsps (aroA:CP4) | Dupont |
| 77 | MIR604 × TC1507 | SYN-IR6Ø4-5 × DAS-Ø15Ø7-1 | | IR (Col)/mcry3a<br>IR (BL)/cry1Fa2<br>HT (Glu)/pat | Syngenta |
| 78 | MON801 (MON80100) | MON801 | | IR (BL)/cry1Ab | Monsanto |
| 79 | MON802 | MON-8Ø2ØØ-7 | | IR (BL)/cry1Ab | Monsanto |
| 80 | MON809 | PH-MON-8Ø9-2 | | IR (BL)/cry1Ab | Monsanto & Dupont |
| 81 | MON810 | MON-ØØ81Ø-6 | YieldGard ™, MaizeGard ™ | IR (BL)/cry1Ab | Monsanto |
| 82 | MON810 × MON88017 | MON-ØØ81Ø-6 × MON-88Ø17-3 | YieldGard ™ VT Triple | IR (BL)/cry1Ab<br>IR (Col)/cry3Bb1<br>HT (Gly)/cp4 epsps (aroA:CP4) | Monsanto |
| 83 | MON832 | | Roundup Ready ™ Maize | HT (Gly)/gov247<br>HT (Gly)/cp4 epsps (aroA:CP4) | Monsanto |
| 84 | MON863 | MON-ØØ863-5 | YieldGard ™ Rootworm RW, MaxGard ™ | IR (Col)/cry3Bb1 | Monsanto |
| 85 | MON863 × MON810 | MON-ØØ863-5 × MON-ØØ81Ø-6 | YieldGard ™ Plus | IR (BL)/cry1Ab<br>IR (Col)/cry3Bb1 | Monsanto |
| 86 | MON863 × MON810 × NK603 | MON-ØØ6Ø3-6 × MON-ØØ81Ø-6 × MON-ØØ863-5 | YieldGard ™ Plus with RR | IR (BL)/cry1Ab<br>IR (Col)/cry3Bb1<br>HT (Gly)/cp4 epsps (aroA:CP4) | Monsanto |

TABLE B-continued

Events, traits, genes, and developing companies of Zea mays plants and/or propagation material. Explanations for abbreviations are listed in Table C.

| No | Event Name | Event Code | Tradename | Trait (Trait type)/ Gene | Developing/ Producing Company |
|---|---|---|---|---|---|
| 87 | MON863 × NK603 | MON-ØØ863-5 × MON-ØØ6Ø3-6 | YieldGard ™ RW + RR | IR (Col)/cry3Bb1<br>HT (Gly)/cp4 epsps (aroA:CP4) | Monsanto |
| 88 | MON87411 | MON-87411-9 | | IR (Col)/cry3Bb1<br>HT (Gly)/cp4 epsps (aroA:CP4)<br>IR (Rw)/dvsnf7 | Monsanto |
| 89 | MON87427 | MON-87427-7 | Roundup Ready ™ Maize | HT (Gly)/cp4 epsps (aroA:CP4) | Monsanto |
| 90 | MON87427 × MON89034 × MON88017 | MON-87427-7 × MON-89Ø34-3 × MON-88Ø17-3 | | HT (Gly)/cp4 epsps (aroA:CP4)<br>IR (BL)/cry2Ab2<br>IR (BL)/cry1A.105<br>IR (Col)/cry3Bb1 | Monsanto |
| 91 | MON87427 × MON89034 × NK603 | MON-87427-7 × MON-89Ø34-3 × MON-ØØ6Ø3-6 | | HT (Gly)/cp4 epsps (aroA:CP4)<br>IR (BL)/cry2Ab2<br>IR (BL)/cry1A.105 | Monsanto |
| 92 | MON87427 × MON89034 × TC1507 × MON88017 × 59122 | MON-87427-7 × MON-89Ø34-3 × DAS-Ø15Ø7-1 × MON-88Ø17-3 × DAS-59122-7 | | HT (Gly)/cp4 epsps (aroA:CP4)<br>IR (Col)/cry34Ab1<br>IR (Col)/cry35Ab1<br>IR (BL)/cry1Fa2<br>HT (Glu)/pat<br>IR (BL)/cry2Ab2 | Monsanto |
| 93 | MON87460 | MON-8746Ø-4 | Genuity ® DroughtGard ™ | Y&S (DT)/cspB | Monsanto & BASF |
| 94 | MON87460 × MON89034 × MON88017 | MON-8746Ø-4 × MON-89Ø34-3 × MON-88Ø17-3 | Genuity ® Drought GardTM with VT Triple PRO | Y&S (DT)/cspB<br>IR (BL)/cry1A.105<br>IR (BL)/cry2Ab2<br>IR (Col)/cry3Bb1<br>HT (Gly)/cp4 epsps (aroA:CP4) | Monsanto |
| 95 | MON87460 × MON89034 × NK603 | MON-8746Ø-4 × MON-89Ø34-3 × MON-ØØ6Ø3-6 | Genuity ® Drought Gard ™ with VT Double PRO | Y&S (DT)/cspB<br>IR (BL)/cry1A.105<br>IR (BL)/cry2Ab2<br>HT (Gly)/cp4 epsps (aroA:CP4) | Monsanto |
| 96 | MON87460 × NK603 | MON-8746Ø-4 × MON-ØØ6Ø3-6 | | Y&S (DT)/cspB<br>HT (Gly)/cp4 epsps (aroA:CP4) | Monsanto |
| 97 | MON88017 | MON-88Ø17-3 | YieldGard ™ VT ™ Rootworm ™ RR2 | IR (Col)/cry3Bb1<br>HT (Gly)/cp4 epsps (aroA:CP4) | Monsanto |
| 98 | MON89034 | MON-89Ø34-3 | YieldGard ™ VT Pro ™ | IR (BL)/cry1A.105<br>IR (BL)/cry2Ab2 | Monsanto |
| 99 | MON89034 × 59122 | MON-89Ø34-3 × DAS-59122-7 | | HT (Glu)/pat<br>IR (Col)/cry34Ab1<br>IR (Col)/cry35Ab1<br>IR (BL)/cry1A.105<br>IR (BL)/cry2Ab2 | Monsanto |
| 100 | MON89034 × 59122 × MON88017 | MON-89Ø34-3 × DAS-59122-7 × MON-88Ø17-3 | | HT (Glu)/pat<br>IR (Col)/cry34Ab1<br>IR (Col)/cry35Ab1<br>IR (Col)/cry3Bb1<br>HT (Gly)/cp4 epsps (aroA:CP4)<br>IR (BL)/cry1A.105<br>IR (BL)/cry2Ab2 | Monsanto |
| 101 | MON89034 × MON88017 | MON-89Ø34-3 × MON-88Ø17-3 | Genuity ® VT Triple Pro ™ | IR (BL)/cry1A.105<br>IR (BL)/cry2Ab2<br>IR (Col)/cry3Bb1<br>HT (Gly)/cp4 epsps (aroA:CP4) | Monsanto |
| 102 | MON89034 × NK603 | MON-89Ø34-3 × MON-ØØ6Ø3-6 | Genuity ® VT Double Pro ™ | IR (BL)/cry1A.105<br>IR (BL)/cry2Ab2<br>HT (Gly)/cp4 epsps (aroA:CP4) | Monsanto |
| 103 | MON89034 × TC1507 | MON-89Ø34-3 × DAS-Ø15Ø7-1 | | IR (BL)/cry1A.105<br>IR (BL)/cry2Ab2<br>IR (BL)/cry1Fa2<br>HT (Glu)/pat | Monsanto |

TABLE B-continued

Events, traits, genes, and developing companies of Zea mays plants and/or propagation material. Explanations for abbreviations are listed in Table C.

| No | Event Name | Event Code | Tradename | Trait (Trait type)/Gene | Developing/Producing Company |
|---|---|---|---|---|---|
| 104 | MON89034 × TC1507 × 59122 | MON-89Ø34-3 × DAS-Ø15Ø7-1 × DAS-59122-7 | | HT (Glu)/pat<br>IR (Col)/cry34Ab1<br>IR (Col)/cry35Ab1<br>IR (BL)/cry1A.105<br>IR (BL)/cry2Ab2<br>IR (BL)/cry1Fa2 | Monsanto |
| 105 | MON89034 × TC1507 × MON88017 | MON-89Ø34-3 × DAS-Ø15Ø7-1 × MON-88Ø17-3 | | IR (Col)/cry3Bb1<br>HT (Gly)/cp4 epsps (aroA:CP4)<br>IR (BL)/cry1A.105<br>IR (BL)/cry2Ab2<br>IR (BL)/cry1Fa2<br>HT (Glu)/pat | Monsanto & Dow |
| 106 | MON89034 × TC1507 × MON88017 × 59122 | MON-89Ø34-3 × DAS-Ø15Ø7-1 × MON-88Ø17-3 × DAS-59122-7 | Genuity ® SmartStax ™ | HT (Glu)/pat<br>IR (Col)/cry34Ab1<br>IR (Col)/cry35Ab1<br>IR (Col)/cry3Bb1<br>HT (Gly)/cp4 epsps (aroA:CP4)<br>IR (BL)/cry1A.105<br>IR (BL)/cry2Ab2<br>IR (BL)/cry1Fa2 | Monsanto & Dow |
| 107 | MON89034 × TC1507 × MON88017 × 59122 × DAS40278 | MON-89Ø34-3 × DAS-Ø15Ø7-1 × MON-88Ø17-3 × DAS-59122-7 × DAS-4Ø278-9 | SmartStax Enlist ™ | HT (Glu)/pat<br>IR (Col)/cry34Ab1<br>IR (Col)/cry35Ab1<br>IR (Col)/cry3Bb1<br>HT (Gly)/cp4 epsps (aroA:CP4)<br>IR (BL)/cry1A.105<br>IR (BL)/cry2Ab2<br>IR (BL)/cry1Fa2<br>HT (2,4-D)/aad1 | Dow |
| 108 | MON89034 × TC1507 × MON88017 × DAS40278 | MON-89Ø34-3 × DAS-Ø15Ø7-1 × MON-88Ø17-3 × DAS-4Ø278-9 | | IR (Col)/cry3Bb1<br>HT (Gly)/cp4 epsps (aroA:CP4)<br>IR (BL)/cry1A.105<br>IR (BL)/cry2Ab2<br>IR (BL)/cry1Fa2<br>HT (Glu)/pat<br>HT (2,4-D)/aad1 | Dow |
| 109 | MON89034 × TC1507 × NK603 | MON-89Ø334-3 × DAS-Ø15Ø7-1 × MON-ØØ6Ø3-6 | Power Core ™ | IR (BL)/cry1A.105<br>IR (BL)/cry2Ab2<br>IR (BL)/cry1Fa2<br>HT (Gly)/cp4 epsps (aroA:CP4)<br>HT (Glu)/pat | Monsanto & Dow |
| 110 | MON89034 × TC1507 × NK603 × DAS40278 | MON-89Ø34-3 × DAS-Ø15Ø7-1 × MON-ØØ6Ø3-6 × DAS-4Ø278-9 | Power Core Enlist ™ | IR (BL)/cry1A.105<br>IR (BL)/cry2Ab2<br>IR (BL)/cry1Fa2<br>HT (Gly)/cp4 epsps (aroA:CP4)<br>HT (Glu)/pat<br>HT (2,4-D)/aad1 | Dow |
| 111 | MS3 | ACS-ZMØØ1-9 | InVigor ™ Maize | PC (MS)/barnase | Bayer Crop Science |
| 112 | MS6 | ACS-ZMØØ5-4 | InVigor ™ Maize | PC (MS)/barnase | Bayer Crop Science |
| 113 | NK603 | MON-ØØ6Ø3-6 | Roundup Ready ™ 2 Maize | HT (Gly)/cp4 epsps (aroA:CP4) | Monsanto |
| 114 | NK603 × MON810 × 4114 × MIR 604 | MON-00603-6 × MON-00810-6 × DP004114-3 × SYN-IR604-4 | | HT (Gly)/cp4 epsps (aroA:CP4)<br>IR (BL)/cry1Ab<br>IR (BL)/cry1F<br>IR (Col)/cry34Ab1<br>IR (Col)/cry35Ab1<br>IR (Col)/mcry3A<br>HT (Glu)/pat | Syngenta & Monsanto |
| 115 | NK603 × MON810 | MON-ØØ6Ø3-6 × MON-ØØ81Ø-6 | YieldGard ™ CB + RR | IR (BL)/cry1Ab<br>HT (Gly)/cp4 epsps (aroA:CP4) | Monsanto |
| 116 | NK603 × T25 | MON-ØØ6Ø3-6 × ACS-ZMØØ3-2 | Roundup Ready ™ Liberty Link ™ Maize | HT (Gly)/cp4 epsps (aroA:CP4)<br>HT (Glu)/pat (syn) | Monsanto |

TABLE B-continued

Events, traits, genes, and developing companies of *Zea mays* plants and/or propagation material. Explanations for abbreviations are listed in Table C.

| No | Event Name | Event Code | Tradename | Trait (Trait type)/ Gene | Developing/ Producing Company |
|---|---|---|---|---|---|
| 117 | T14 | ACS-ZMØØ2-1 | Liberty Link ™ Maize | HT (Glu)/pat (syn) | Bayer Crop Science |
| 118 | T25 | ACS-ZMØØ3-2 | Liberty Link ™ Maize | HT (Glu)/pat (syn) | Bayer Crop Science |
| 119 | T25 × MON810 | ACS-ZMØØ3-2 × MON-ØØ81Ø-6 | Liberty Link ™ Yieldgard ™ Maize | IR (BL)/cry1Ab<br>HT (Glu)/pat (syn) | Bayer Crop Science & Monsanto |
| 120 | TC1507 | DAS-Ø15Ø7-1 | Herculex ™ I, Herculex ™ CB | IR (BL)/cry1Fa2<br>HT (Glu)/pat | Dow & Dupont |
| 121 | TC1507 × 59122 × MON810 × MIR604 × NK603 | DAS-Ø15Ø7-1 × DAS-59122-7 × MON-ØØ81Ø-6 × SYN-IR6Ø4-5 × MON-ØØ6Ø3-6 | Optimum ™ Intrasect Xtreme | IR (BL)/cry1Fa2<br>HT (Glu)/pat<br>IR (Col)/cry34Ab1<br>IR (Col)/cry35Ab1<br>IR (Col)/mcry3A | Dupont |
| 122 | TC1507 × MON810 × MIR604 × NK603 | DAS-Ø15Ø7-1 × MON-ØØ81Ø-6 × SYN-IR6Ø4-5 × MON-ØØ6Ø3-6 | | IR (Col)/mcry3A<br>IR (BL)/cry1Fa2<br>HT (Glu)/pat<br>IR (BL)/cry1Ab<br>HT (Gly)/cp4 epsps (aroA:CP4) | Dupont |
| 123 | TC1507 × 59122 | DAS-Ø15Ø7-1 × DAS-59122-7 | Herculex XTRA ™ | IR (BL)/cry1Fa2<br>HT (Glu)/pat<br>IR (Col)/cry34Ab1<br>IR (Col)/cry35Ab1 | Dow & Dupont |
| 124 | TC1507 × 59122 × MON810 | DAS-Ø15Ø7-1 × DAS-59122-7 × MON-ØØ81Ø-6 | | IR (BL)/cry1Fa2<br>HT (Glu)/pat<br>IR (Col)/cry34Ab1<br>IR (Col)/cry35Ab1<br>IR (BL)/cry1Ab | Dupont |
| 125 | TC1507 × 59122 × MON810 × NK603 | DAS-Ø15Ø7-1 × DAS-59122-7 × MON-ØØ81Ø-6 × MON-ØØ6Ø3-6 | Optimum ™ Intrasect XTRA | IR (BL)/cry1Fa2<br>HT (Glu)/pat<br>IR (Col)/cry34Ab1<br>IR (Col)/cry35Ab1<br>HT (Gly)/cp4 epsps (aroA:CP4)<br>IR (BL)/cry1Ab | Dupont |
| 126 | TC1507 × 59122 × MON88017 | DAS-Ø15Ø7-1 × DAS-59122-7 × MON-88Ø17-3 | | IR (BL)/cry1Fa2<br>HT (Glu)/pat<br>IR (Col)/cry34Ab1<br>IR (Col)/cry35Ab1<br>IR (Col)/cry3Bb1<br>HT (Gly)/cp4 epsps (aroA:CP4) | Monsanto & Dow |
| 127 | TC1507 × 59122 × NK603 | DAS-Ø15Ø7-1 × DAS-59122-7 × MON-ØØ6Ø3-6 | Herculex XTRA ™ RR | IR (BL)/cry1Fa2<br>HT (Glu)/pat<br>IR (Col)/cry34Ab1<br>IR (Col)/cry35Ab1<br>HT (Gly)/cp4 epsps (aroA:CP4) | Dow & Dupont |
| 128 | TC1507 × GA21 | DAS-Ø15Ø7-1 × MON-ØØØ21-9 | | IR (BL)/cry1Fa2<br>HT (Glu)/pat<br>HT (Gly)/mepsps | Dupont |
| 129 | TC1507 × MIR604 × NK603 | DAS-Ø15Ø7-1 × SYN-IR6Ø4-5 × MON-ØØ6Ø3-6 | Optimum ™ TRIsect | IR (BL)/cry1Fa2<br>HT (Glu)/pat<br>HT (Gly)/cp4 epsps (aroA:CP4)<br>IR (Col)/mcry3A | Dupont |
| 130 | TC1507 × MON810 | DAS-Ø15Ø7-1 × MON-ØØ81Ø-6 | | IR (BL)/cry1Fa2<br>HT (Glu)/pat<br>IR (BL)/cry1Ab | Dow & Dupont |
| 131 | TC1507 × MON810 × MIR162 × NK603 | DAS-Ø15Ø7-1 × MON-ØØ81Ø-6 × SYN-IR162-4 × MON-ØØ6Ø3-6 | Optimum Leptra ™ | IR (BL)/cry1Fa2<br>HT (Glu)/pat<br>IR (BL)/cry1Ab<br>HT (Gly)/cp4 epsps (aroA:CP4)<br>IR (BL)/vip3Aa20 | Dupont |
| 132 | TC1507 × MON810 × NK603 | DAS-Ø15Ø7-1 × MON-ØØ81Ø-6 × MON-ØØ6Ø3-6 | Optimum ™ Intrasect | IR (BL)/cry1Fa2<br>HT (Glu)/pat<br>IR (BL)/cry1Ab<br>HT (Gly)/cp4 epsps (aroA:CP4) | Dupont |

TABLE B-continued

Events, traits, genes, and developing companies of Zea mays plants and/or propagation material. Explanations for abbreviations are listed in Table C.

| No | Event Name | Event Code | Tradename | Trait (Trait type)/Gene | Developing/Producing Company |
|---|---|---|---|---|---|
| 133 | TC1507 × MON88017 | DAS-Ø15Ø7-1 × MON-88Ø17-3 | | IR (BL)/cry1Fa2<br>HT (Glu)/pat<br>IR (Col)/cry3Bb1<br>HT (Gly)/cp4 epsps (aroA:CP4) | Monsanto |
| 134 | TC1507 × NK603 | DAS-Ø15Ø7-1 × MON-ØØ6Ø3-6 | Herculex ™ I RR | IR (BL)/cry1Fa2<br>HT (Glu)/pat<br>HT (Gly)/cp4 epsps (aroA:CP4) | Dow |
| 135 | TC6275 | DAS-Ø6275-8 | | IR (BL)/mocry1F<br>HT (Glu)/bar | Dow |
| 136 | VCO-Ø1981-5 | VCO-Ø1981-5 | | HT (Gly)/epsps grg23ace5 | Genective S.A. |
| 137 | DK404SR | DK404SR | | HT (Cyc)/ACCase (mutant) | BASF |
| 138 | EXP1910IT | EXP1910IT | | HT (Imi)/als (mutant) | Syngenta |
| 139 | 3272 × Bt11 × MIR604 × TC1507 × 5307 × GA21 | SYN-E3272-5 × SYN-BTØ11-1 × SYN-IR6Ø4-5 × DAS-Ø15Ø7-1 × SYN-Ø53Ø7-1 × MON-ØØØ21-9 | Agrisure Duracade ™ E-Z Refuge ™ 5122 | IR (BL)/cry1Ab<br>IR (Col)/mcry3A<br>IR (BL)/cry1Fa2<br>IR (Col)/ecry3.1Ab<br>HT (Glu)/pat<br>HT (Gly)/mepsps | Syngenta |
| 140 | MIR162 × NK603 | SYN-IR162-4 × MON-ØØ6Ø3-6 | | IR (BL)/vip3Aa20<br>HT (Gly)/cp4 epsps (aroA:CP4) | Syngenta |
| 141 | MON810 × MIR162 | MON-ØØ81Ø-6 × SYN-IR162-4 | | IR (BL)/cry1Ab<br>IR (BL)/vip3Aa20 | Monsanto |
| 142 | TC1507 × MIR162 × NK603 | DAS-Ø15Ø7-1 × SYN-IR162-4 × MON-ØØ6Ø3-6 | | IR (BL)/cry1F<br>HT (Glu)/pat<br>IR (BL)/vip3Aa20<br>HT (Gly)/cp4 epsps (aroA:CP4) | Dow |
| 143 | TC1507 × MON810 × MIR162 | DAS-Ø15Ø7-1 × MON-ØØ81Ø-6 × SYN-IR162-4 | | IR (BL)/cry1Fa2<br>HT (Glu)/pat<br>IR (BL)/cry1Ab<br>HT (Gly)/cp4 epsps (aroA:CP4)<br>IR (BL)/vip3Aa20 | Dow |
| 144 | Bt11 × MIR162 × MIR604 × TC1507 × 5307 × GA21 | SYN-BtØ11-1 × SYN-IR162-4 × SYN-IR6Ø4-5 × DAS-Ø15Ø7-1 × SYN-Ø53Ø7-1 × MON-ØØØ21-9 | Agrisure Duracade ™ E-Z Refuge ™ 5222 | HT (Glu)/pat<br>HT (Gly)/mepsps<br>IR (Col)/ecry3.1Ab<br>IR (Col)/mcry3A<br>IR (BL)/cry1Ab<br>IR (BL)/cry1Fa2<br>IR (BL)/vip3Aa20 | Syngenta |
| 145 | TC1507 × MON810 × MIR162 | DAS-Ø15Ø7-1 × MON-ØØ81Ø-6 × SYN-IR162-4 × DAS-Ø15Ø7-1 | Optimum Intrasect Leptra ® | IR (BL)/cry1Fa2<br>IR (BL)/cry1Ab<br>IR (BL)/vip3Aa20<br>HT (Glu)/pat | Dupont |
| 146 | MON87403 | MON874Ø3-1 | | Y&S (Y): Athb17 | Monsanto |
| 147 | MON87419 | MON87419-8 | | HT (Glu)/pat<br>HT (Dic)/dmo | Monsanto |
| 148 | MZHG0JG | SYN-ØØØJG-2 | | HT (Glu)/pat<br>HT (Gly)/2mepsps | Syngenta |
| 149 | MZIR098 | SYN-ØØØ98-3 | | IR (Col)/ecry3.1Ab<br>IR (Col)/mcry3A<br>HT (Glu)/pat | Syngenta |
| 150 | MYDT09Y | | | Y&S (DT) | Syngenta |
| 151 | DP-E29 | | | | Syngenta |

TABLE C explanations for abbreviations in Table B

| TRAIT | TRAIT - full name | TRAIT TYPE | TRAIT TYPE - full name |
|---|---|---|---|
| HT | Herbicide Tolerance | HT (Gly) | glyphosate tolerance |
| | | HT (Glu) | glufosinate tolerance |
| | | HT (2,4-D) | resistance against 2,4-D Choline |
| | | HT (SU) | sulfonylurea tolerance |

TABLE C-continued explanations for abbreviations in Table B

| TRAIT | TRAIT - full name | TRAIT TYPE | TRAIT TYPE - full name |
|---|---|---|---|
| | | HT (Imi) | imidazolinone tolerance |
| | | HT (Dic) | dicamba tolerance |
| | | HT (HPPD) | HPPD inhibitor resistance |
| | | HT (Cyc) | cyclohexanone herbicide tolerance (e.g. sethoxydim) |
| IR | Insect resistance (including Nematodes) | IR (BL) | broad spectrum resistance against lepidopterans (above ground worms) |
| | | IR (Col) | resistance against Coleopterans (beetles) |
| | | IR (Rw) | resistance against root worm |
| Y&S | Yield and Stress | Y&S (Y) | yield increase |
| | | Y&S (DT) | drought tolerance |
| PC | Pollination control and male sterility systems | PC (MS) | male sterility |
| | | PC (FR) | fertility restoration |
| ST | Specialty Trait (includes Feed, Food, Quality) | ST (OIL) | altered oil content |
| | | ST (AA) | altered amino-acid content |
| | | ST (P) | phytase production |
| | | ST (CA) | corn amylase |

Detailed information of the *Zea mays* plants listed in Table B is available online under www.isaaa.org. Traits that are emphasized in particular are the increased defense of the plants against insects, arachnids, nematodes, slugs and snails, preferably against insects, by virtue of toxins formed in the plants, in particular those formed in the plants by expression of genes of *Bacillus thuringiensis* (for example by the genes cry1Aa, cry1Ab, cry1Ac, cry2A, cry3A, cry3B2, cry9c, cry2Ab, cry3Bb, cry1F, and vip3Aa20), or of genes derived from *Bacillus thuringiensis* by mutagenesis, or genetic engineering (for examples the genes ecry3, mcry3A, mocry1F), and also combinations thereof) (referred to herein as "Bt plants").

In one embodiment, insect resistance is provided by at least one gene of *Bacillus thuringiensis*. In another embodiment, insect resistance is provided by at least one gene derived from a *Bacillus thuringiensis* gene by mutagenesis, or genetic engineering. In one embodiment, the gene derived from the *Bacillus thuringiensis* gene may have at least one base mutation that causes at least on amino acid exchange, wherein both exchanges are in comparison with the respective wild type sequence of the gene, or protein. In another embodiment, the gene derived from a *Bacillus thuringiensis* gene may be truncated with regard to the wild type sequence by up to 30 base pairs, preferably by up to 150 base pairs, and most preferably by up to 500 base pairs.

In one embodiment, the trait is conveyed by at least one gene selected from cry1Aa, cry1Ab, cry1Ac, cry2A, cry3A, cry3B2, cry9c, cry2Ab, cry3Bb and cry1F, and combinations thereof. In another embodiment, the trait is conveyed by at least one gene selected from cry1Aa, cry1Ab, cry1A.105, cry1F, cry1Fa2, cry2Ab2, cry2Ae, cry3Bb1, cry3Bb1, cry34Ab1, cry35Ab1, cry9c, dvsnf7, ecry3.1Ab, mcry3A, mocry1F, pin2, vip3Aa20, and combinations thereof, preferably Cry3Bb1, Cry34Ab1, Cry35Ab1, Ecry3.1Ab, Mcry3A, and combinations thereof. In another embodiment, the trait is conveyed by at least one gene selected from cry1A, cry1Aa, cry1Ab, cry1Ac, cry1A.105, cry1F, cry1Fa2, cry2Ab2, cry2Ae, cry3Bb1, cry3Bb1, cry34Ab1, cry35Ab1, cry9c, dvsnf7, ecry3.1Ab, mcry3A, mocry1F, pin2, vip3Aa20, and combinations thereof. In another embodiment, the trait is conveyed by at least one gene selected from cry1Aa, cry1Ab, cry1A.105, cry1F, cry1Fa2, cry2Ab2, cry2Ae, cry3Bb1, cry3Bb1, cry34Ab1, cry35Ab1, cry9c, dvsnf7, ecry3.1Ab, mcry3A, mcry1F, and combinations thereof. In another embodiment, the trait is conveyed by at least one gene selected from cry1Ab, cry1A.105, cry2Ab2, cry1F, vip3Aa20, and combinations thereof. In another embodiment, the trait is conveyed by cry1Ab and cry1F. In another embodiment, the trait is conveyed by cry1A.105 and cry2AB2. In another embodiment, the trait is conveyed by cry1A.105, cry2AB2, and cry1F. In another embodiment, the trait is conveyed by vip3Aa20 and cry1Ab. In another embodiment, the trait is conveyed by cry1Ab. In another embodiment, the trait is conveyed by cry1A.105. In another embodiment, the trait is conveyed by cry2Ab2. In another embodiment, the trait is conveyed by cry1F. In another embodiment, the trait is conveyed by vip3Aa20.

Traits that are also particularly emphasized are the increased defense of the plants against fungi, bacteria and viruses by systemic acquired resistance, systemin, phytoalexins, elicitors and resistance genes and correspondingly expressed proteins and toxins. Traits that are furthermore particularly emphasized are the increased tolerance of the plants to certain herbicidally active compounds, for example glyphosate, glufosinate, 2,4-D Choline, sulfonylurea, imidazolinone, dicamba, HPPD inhibitor, or cyclohexanone herbicide. Accordingly, the maize plant may have a herbicide tolerance that is conveyed by at least one gene selected from pat, mepsps, cp4 epsps (aroA:CP4), zm-hra, gat4621, bar, aad1, pat (syn), 2mepsps, gov247, epsps grg23ace5, ACCase (mutant), als (mutant), dmo, and combination thereof, preferably cp4 epsps (aroA:CP4). The genes which impart the desired traits in question can also be present in combination with one another in the transgenic plants.

Suitable "Bt maize" are sold under the trade names 32138 SPT maintainer, Enogen™, Agrisure™ Duracade™ Agrisure® Duracade™ 5122, Agrisure® Duracade™ 5222, Herculex™ RW, Herculex™ RW Roundup Ready™ 2, Optimum™ GAT™, Bt10, Agrisure™ CB/LL, Agrisure® 3122, Agrisure™ GT/CB/LL/TL, Agrisure® Viptera™ 2100, Agrisure® Viptera™ 3110, Agrisure® Viptera™ 3100, Agrisure® Viptera™ 3111, Agrisure™ Viptera™ 4, Agrisure™ Viptera 3220, Agrisure™ CB/LL/RW, Agrisure™ 3000GT, NaturGard KnockOut™, Maximizer™, Starlink™

Maize, Enlist™ Maize, Bt Xtra™ Maize, Roundup Ready™ Maize, Agrisure™ GT, Roundup Ready™ YieldGard™ maize, Mavera™ Maize, Mavera™ YieldGard™ Maize, Agrisure™, YieldGard™, MaizeGard™, YieldGard™ VT Triple, Roundup Ready™ Maize, YieldGard™ Rootworm RW, MaxGard™, YieldGard™ Plus, YieldGard™ Plus with RR, YieldGard™ RW+RR, Roundup Ready™ Maize, Genuity® DroughtGard™, YieldGard™ VT™ Rootworm™ RR2, YieldGard™ VT Pro™, Genuity® VT Triple Pro™, Genuity® VT Double Pro™, Genuity® SmartStax™, Power Core™, InVigor™ Maize, Roundup Ready™ 2 Maize, YieldGard™ CB+RR, Roundup Ready™ Liberty Link™ Maize, Liberty Link™ Yieldgard™ Maize, Herculex™ I, Herculex™ CB, Optimum™ Intrasect Xtreme, Herculex XTRA™, Optimum™ Intrasect XTRA, Herculex XTRA™ RR, Optimum™ TRIsect, Optimum™ Intrasect, Herculex™ I RR, preferably those which carry an insect resistance gene. Preferred maize cultivars are sold under the trade names of Optimum™ Intrasect™, Yieldgard™ VT Pro™, Power Core™, Agrisure Viptera™, Roundup Ready™ Yieldgard™, Agrisure™ TL, Herculex™ I, and Herculex™ CB. The plants usually have a genetic event name selected from 33121, 4114, 5307, 59122, Bt10, Bt11, Bt176 (176), CBH-351, DBT418, MIR162, MIR604, MON801 (MON80100), MON802, MON809, MON810, MON863, MON87411, MON88017, MON89034, MZIR098, TC1507, TC6275, and combinations thereof. Preferably, the plants have a genetic event name selected from 4114, 5307, 59122, MIR604, MON863, MON87411, MON88017, MZIR098, and combinations thereof, most preferably NK603.

In one embodiment, the methods and uses of the invention relate to maize plants as described in Table B, rows 44-47, 49, 68, 98, 109, 121, 125, and 132. In another embodiment, the methods and uses of the invention relate to maize plants as described in Table B, rows 44-47, 49, and 68. In another embodiment, the methods and uses of the invention relate to maize plants as described in Table B, rows 109. In another embodiment, the methods and uses of the invention relate to maize plants as described in Table B, rows 98. In another embodiment, the methods and uses of the invention relate to maize plants as described in Table B, rows 121, 125, and 132.

The components of the ginkgo tree, or the pesticidal compositions comprising them are used to control pests of a maize plant by contacting the maize plant, parts of it, or its plant propagation material, the pests, their food supply, habitat, or breeding grounds with a pesticidally effective amount of components of the ginkgo tree. In one embodiment, application of the components of the ginkgo tree is on the maize plant, parts of it, or its propagation material. In another embodiment, application of the components of the ginkgo tree is on the maize plant. In yet another embodiment, application of the components of the ginkgo tree is on propagation material of maize plants. In another embodiment, application of the components of the ginkgo tree is to the locus of the maize plant. Application may be before infestation, or when the pest is present. Application of the components of the ginkgo tree can be performed according to any of the usual modes of application, e.g. foliar, drench, soil, in furrow, seed treatment etc. In one embodiment, the components of the ginkgo tree are applied by soil drench application. In another embodiment, the components of the ginkgo tree are applied for protecting plant propagation material, preferably by seed-treatment to seeds of maize crops. In yet another embodiment, the components of the ginkgo tree are applied by in-furrow treatment. In yet another embodiment, the components of the ginkgo tree are applied by foliar application.

The components of the ginkgo tree may be applied in combination with an attractant. An attractant is a chemical that causes the insect to migrate towards the location of application. For control of stinkbugs it can be advantageous to apply the components of the ginkgo tree with an attractant, particularly when the application is foliar. Pentatomidae are often located near to the ground, and application of an attractant may encourage migration up the plant towards the active ingredient. Suitable attractants include glucose, saccharose, salt, glutamate, citric acid, soybean oil, peanut oil and soybean milk. Glutamate and citric acid are of particular interest, with citric acid being preferred. An attractant may be premixed with the components of the ginkgo tree prior to application, e.g. as a readymix, or tankmix, or by simultaneous application, or sequential application to the plant. Suitable rates of attractants are for example 0.02 kg/ha-3 kg/ha. The components of the ginkgo tree are preferably used for pest control at 1-500 g/ha, preferably 10-100 g/ha.

The components of the ginkgo tree may be applied in the methods of the present invention in mixtures with fertilizers (for example nitrogen-, potassium- or phosphorus-containing fertilizers). Suitable formulation types include granules of fertilizer. The mixtures preferably contain up to 25% by weight of the components of the ginkgo tree.

The components of the ginkgo tree may be mixed with other compounds having biological activity, for example micronutrients, or compounds having fungicidal activity, or which possess plant growth regulating, herbicidal, insecticidal, nematicidal, or acaricidal activity.

The components of the ginkgo tree applied in the disclosed uses and methods of application may be the sole active ingredient of the composition, or they may be admixed with one or more additional active ingredients such as an insecticide, fungicide, synergist, herbicide, or plant growth regulator where appropriate. An additional active ingredient may: provide a composition having a broader spectrum of activity, or increased persistence at a locus; synergize the activity, or complement the activity (for example by increasing the speed of effect, or overcoming repellency) of the components of the ginkgo tree; or help to overcome, or prevent the development of resistance to individual components. The particular additional active ingredient will depend upon the intended utility of the composition.

According to one embodiment of the present invention, individual components of the composition according to the invention such as parts of a kit, or parts of a binary, or ternary mixture may be mixed by the user himself in a spray tank and further auxiliaries may be added, if appropriate.

The components of the ginkgo tree may be mixed with soil, peat, or other rooting media for the protection of plants against seed-borne, soil-borne, or foliar fungal diseases. Examples of suitable synergists for use in the compositions include piperonyl butoxide, sesamex, safroxan and dodecyl imidazole. Suitable herbicides and plant-growth regulators for inclusion in the compositions will depend upon the intended target and the effect required. Preferably, the components of the ginkgo tree are mixed with a herbicide. Examples of herbicides are glyphosate, gluphosinate, sulfonylurea, imidazoline, or a HPPD inhibitor.

The components of the ginkgo tree may be present in form of agrochemical compositions comprising one, or more auxiliary agents and at least one component of the ginkgo tree and/or one of its individual embodiments, which are applied in the methods of the present invention. An agrochemical composition comprises a pesticidally effective amount of the components of the ginkgo tree and/or one of its individual embodiments. An agrochemical composition comprises a pesticidally effective amount of the components of the ginkgo tree. The term "pesticidally effective amount" is defined below.

The components of the ginkgo tree can be converted into customary types of agro-chemical compositions, e.g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders, or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, 6th Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005. Suitable auxiliaries are solvents, liquid carriers, solid carriers, or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders. Suitable solvents and liquid carriers are water and organic solvents, such as mineral oil fractions of medium to high boiling point, e.g. kerosene, diesel oil; oils of vegetable, or animal origin; aliphatic, cyclic and aromatic hydrocarbons, e. g. toluene, paraffin, tetrahydronaphthalene, alkylated naphthalenes; alcohols, e.g. ethanol, propanol, butanol, benzyl alcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylaryl sulfonates, diphenylsulfonates, alpha-olefin sulfonates, lignin sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates. Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters that have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinyl pyrrolidone, vinyl alcohols, or vinyl acetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a negligible or even no pesticidal activity themselves, and which improve the biological performance of the components of the ginkgo tree on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), inorganic clays (organically modified or unmodified), polycarboxylates, and silicates. Suitable bactericides are bronopol and isothiazolinone derivatives such as alkylisothiazolinones and benzisothiazolinones. Suitable anti-freezing agents are ethylene glycol, propylene glycol, urea and glycerin. Suitable anti-foaming agents are silicones, long chain alcohols, and salts of fatty acids. Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants). Suitable tackifiers or binders are polyvinylpyrrolidons, polyvinylacetates, polyvinylalcohols, polyacrylates, biological or synthetic waxes, and cellulose ethers.

Examples for composition types and their preparation are:
i) Water-soluble concentrates (SL, LS): 10-60 wt % of the components of the ginkgo tree and 5-15 wt % wetting agent (e.g. alcohol alkoxylates) are dissolved in water and/or in a water-soluble solvent (e.g. alcohols) up to 100 wt %. The active substance dissolves upon dilution with water.

ii) Dispersible concentrates (DC): 5-25 wt % of a components of the ginkgo tree and 1-10 wt % dispersant (e.g. polyvinylpyrrolidone) are dissolved in up to 100 wt % organic solvent (e.g. cyclohexanone). Dilution with water gives a dispersion.

iii) Emulsifiable concentrates (EC): 15-70 wt % of the components of the ginkgo tree and 5-10 wt % emulsifiers (e.g. calcium dodecylbenzenesulfonate and castor oil ethoxylate) are dissolved in up to 100 wt % water-insoluble organic solvent (e.g. aromatic hydrocarbon). Dilution with water gives an emulsion.

iv) Emulsions (EW, EO, ES): 5-40 wt % of the components of the ginkgo tree and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into up to 100 wt % water by means of an emulsifying machine and made into a homogeneous emulsion. Dilution with water gives an emulsion.

v) Suspensions (SC, OD, FS): in an agitated ball mill, 20-60 wt % of the components of the ginkgo tree are comminuted with addition of 2-10 wt % dispersants and wetting agents (e.g. sodium lignosulfonate and alcohol ethoxylate), 0.1-2 wt % thickener (e.g. xanthan gum) and up to 100 wt % water to give a fine active substance suspension. Dilution with water gives a stable suspension of the active sub-stance. For FS type composition up to 40 wt % binder (e.g. polyvinylalcohol) is added.

vi) Water-dispersible granules and water-soluble granules (WG, SG): 50-80 wt % of the components of the ginkgo tree are ground finely with addition of up to 100 wt % dispersants and wetting agents (e.g. sodium lignosulfonate and alcohol ethoxylate) and prepared as water-dispersible or water-soluble granules by means of technical appliances (e. g. extrusion, spray tower, fluidized bed). Dilution with water gives a stable dispersion or solution of the active substance.

vii) Water-dispersible powders and water-soluble powders (WP, SP, WS): 50-80 wt % of the components of the ginkgo tree are ground in a rotor-stator mill with ad-dition of 1-5 wt % dispersants (e.g. sodium lignosulfonate), 1-3 wt % wetting agents (e.g. alcohol ethoxylate) and up to 100 wt % solid carrier, e.g. silica gel. Dilution with water gives a stable dis-persion or solution of the active substance.

viii) Gel (GW, GF): in an agitated ball mill, 5-25 wt % of the components of the ginkgo tree are comminuted with addition of 3-10 wt % dispersants (e.g. sodium lignosulfonate), 1-5 wt % thickener (e.g. carboxymethylcellulose) and up to 100 wt % water to give a fine suspension of the active sub-stance. Dilution with water gives a stable suspension of the active substance.

ix) Microemulsion (ME): 5-20 wt % of the components of the ginkgo tree are added to 5-30 wt % organic solvent blend (e.g. fatty acid dimethylamide and cyclohexanone), 10-25 wt % surfactant blend (e.g. alcohol ethoxylate and arylphenol ethoxylate), and water up to 100%. This mixture is stirred for 1 h to produce spontaneously a thermodynamically stable microemulsion.

x) Microcapsules (CS): an oil phase comprising 5-50 wt % of the components of the ginkgo tree, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of the components of the ginkgo tree, 0-40 wt % water insoluble organic solvent (e.g. aromatic hydrocarbon), and an isocyanate monomer (e.g. diphenylme-thene-4,4'-diisocyanatae) are dispersed into an aqueous solution of a protective colloid (e.g. polyvinyl alcohol). The addition of a polyamine (e.g. hexamethylenediamine) results in the formation of a polyurea microcapsule. The monomers amount to 1-10 wt %. The wt % relate to the total CS composition.

xi) Dustable powders (DP, DS): 1-10 wt % of the components of the ginkgo tree are ground finely and mixed intimately with up to 100 wt % solid carrier, e.g. finely divided kaolin.

xii) Granules (GR, FG): 0.5-30 wt % of the components of the ginkgo tree is ground finely and associated with up to 100 wt % solid carrier (e.g. silicate). Granulation is achieved by extrusion, spray-drying or the fluidized bed.

xiii) Ultra-low volume liquids (UL): 1-50 wt % of the components of the ginkgo tree are dissolved in up to 100 wt % organic solvent, e.g. aromatic hydrocarbon.

The compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate.

In a further embodiment, either individual components of the composition according to the invention or partially premixed components, e. g. components comprising components of the ginkgo tree (or one of its individual embodiments) and/or future active substances may be mixed by the user in a spray tank and further auxiliaries and additives may be added, if appropriate. In a further embodiment, either individual components of the composition according to the invention or partially premixed components can be applied jointly (e.g. after tank mix) or consecutively.

The compounds of the present invention are effective through both contact and ingestion. Furthermore, the compounds of the present invention can be applied to any and all developmental stages, such as egg, larva, pupa, and adult.

The compounds of the present invention can be applied as such or in form of compositions comprising them as defined above. Furthermore, the compounds of the present invention can be applied together with a mixing partner as defined above or in form of compositions comprising said mixtures as defined above. The components of said mixture can be applied simultaneously, jointly or separately, or in succession, that is immediately one after another and thereby creating the mixture "in situ" on the desired location, e.g. the plant, the sequence, in the case of separate application, generally not having any effect on the result of the control measures.

The application can be carried out both before and after the infestation of the crops, plants, plant propagation materials, such as seeds, soil, or the area, material or environment by the pests.

Suitable application methods include inter alia soil treatment, seed treatment, in furrow application, and foliar application. Soil treatment methods include drenching the soil, drip irrigation (drip application onto the soil), dipping roots, tubers or bulbs, or soil injection. Seed treatment techniques include seed dressing, seed coating, seed dusting, seed soaking, and seed pelleting. In furrow applications typically include the steps of making a furrow in cultivated land, seeding the furrow with seeds, applying the pesticidally active compound to the furrow, and closing the furrow. Foliar application refers to the application of the pesticidally active compound to plant foliage, e.g. through spray equipment. For foliar applications, it can be advantageous to modify the behavior of the pests by use of pheromones in combination with the compounds of the present invention. Suitable pheromones for specific crops and pests are known to a skilled person and publicly available from databases of pheromones and semiochemicals, such as http://www.pherobase.com.

As used herein, the term "contacting" includes both direct contact (applying the compounds/compositions directly on the animal pest or plant—typically to the foliage, stem or roots of the plant) and indirect contact (applying the compounds/compositions to the locus, i.e. habitat, breeding ground, plant, seed, soil, area, material or environment in which a pest is growing or may grow, of the animal pest or plant).

The term "controlling" comprises both the combating of pests that have infested a maize plant, and preventing the future infestation of the maize plant. Preferably, controlling refers to the combating of pests that have infested a maize plant.

The term "animal pest" includes arthropods, gastropods, and nematodes. Preferred animal pests according to the invention are arthropods, preferably insects and arachnids, in particular insects. Insects, which are of particular relevance for crops, are typically referred to as crop insect pests.

The term "crop" refers to both, growing and harvested crops.

The term "plant propagation material" refers to all the generative parts of the plant such as seeds and vegetative plant material such as cuttings, which can be used for the multiplication of the plant. This includes seeds, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

Suitable seeds for the uses and methods of application are grains of maize plants, which are also referred to as kernel.

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

In the case of soil treatment, or in furrow application, the quantity of active ingredient ranges from 0.0001 to 500 g per 100 m$^2$, preferably from 0.001 to 20 g per 100 m$^2$.

For use in treating crop plants, e.g. by foliar application, the rate of application of the active ingredients of this invention may be in the range of 0.0001 g to 4000 g per hectare, e.g. from 1 g to 2 kg per hectare or from 1 g to 750 g per hectare, desirably from 1 g to 100 g per hectare, more desirably from 10 g to 50 g per hectare, e.g., 10 to 20 g per hectare, 20 to 30 g per hectare, 30 to 40 g per hectare, or 40 to 50 g per hectare.

The components of the ginkgo tree are particularly suitable for use in the treatment of seeds in order to protect the seeds from insect pests, in particular from soil-living insect pests, and the resulting seedling's roots and shoots against soil pests and foliar insects. The present invention therefore also relates to a method for the protection of seeds from insects, in particular from soil insects, and of the seedling's roots and shoots from insects, in particular from soil and foliar insects, said method comprising treating the seeds before sowing and/or after pregermination with components of the ginkgo tree. The protection of the seedling's roots and shoots is preferred. More preferred is the protection of seedling's shoots from piercing and sucking insects, chewing insects and nematodes.

The term "seed treatment" comprises all suitable seed treatment techniques known in the art, such as seed dressing, seed coating, seed dusting, seed soaking, seed pelleting, and in-furrow application methods. Preferably, the seed treatment application of the active compound is carried out by spraying or by dusting the seeds before sowing of the plants and before emergence of the plants.

The present invention also comprises seeds coated with or containing the active compound. The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

In addition, the active compound may also be used for the treatment of seeds from plants, which have been modified by mutagenesis or genetic engineering, and which e.g. tolerate the action of herbicides or fungicides or insecticides. Such modified plants have been described in detail above.

Conventional seed treatment formulations include for example flowable concentrates (FS), solutions (LS), suspoemulsions (SE), powders for dry treatment (DS), water dispersible powders for slurry treatment (WS), water-soluble powders (SS) and emulsion (ES) and (EC) and gel formulation (GF). These formulations can be applied to the seed diluted or undiluted. Application to the seeds is carried out before sowing, either directly on the seeds or after having pregerminated the latter. Preferably, the formulations are applied such that germination is not included.

The active substance concentrations in ready-to-use formulations, which may be obtained after two-to-tenfold dilution, are preferably from 0.01 to 60% by weight, more preferably from 0.1 to 40% by weight.

In a preferred embodiment, a FS formulation is used for seed treatment. Typically, a FS formulation may comprise 1-800 g/l of active ingredient, 1-200 g/l surfactant, 0 to 200 g/l antifreezing agent, 0 to 400 g/l of binder, 0 to 200 g/l of a pigment and up to 1 liter of a solvent, preferably water. Especially preferred FS formulations of the compounds of the present invention for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

In the treatment of seed, the application rates of the components of the ginkgo tree are generally from 0.1 g to 10 kg per 100 kg of seed, preferably from 1 g to 5 kg per 100 kg of seed, more preferably from 1 g to 1000 g per 100 kg of seed and in particular from 1 g to 200 g per 100 kg of seed, e.g. from 1 g to 100 g or from 5 g to 100 g per 100 kg of seed.

The invention therefore also relates to seed comprising components of the ginkgo tree, or an agriculturally useful salt thereof, as defined herein. The amount of the components of the ginkgo tree or the agriculturally useful salt thereof will in general vary from 0.1 g to 10 kg per 100 kg of seed, preferably from 1 g to 5 kg per 100 kg of seed, in particular from 1 g to 1000 g per 100 kg of seed. For specific crops such as lettuce the rate can be higher.

Advantages of the present invention are that the pesticidal activity of the components of the ginkgo tree may be synergistically enhanced by the insecticidal trait of a modified plant, in particular by insecticidal traits conveyed by genes of *Bacillus thuringiensis*. Furthermore, it has been found that the compounds of the present invention are suitable for preventing insects to become resistant to the insecticidal trait, or for combating pests, which already have become resistant to the insecticidal trait of a modified plant. Moreover, the compounds of the present invention are suitable for combating pests, against which the insecticidal trait is not effective, so that the complementary insecticidal activity of the components of the ginkgo tree can advantageously be used.

The following examples illustrate the invention.

EXAMPLES

Bilobalide and ginkgolide A are commercially available (e.g. from Interchim).

Agrisure™ Viptera—corresponding to row 68 in Table B—has insect resistance by virtue of event MIR162.

Roundoup Ready™ 2—corresponding to row 113 in Table B—has herbicide tolerance by virtue of event NK603.

Abbreviations: l is liter, ha is hectare, DAI is day(s) after infestation, DAT is day(s) after treatment with the respective compound, ppm is parts per million.

Relative efficacy (E) values were calculated according to Abbot's formula $E=[(C-G)/C] \times 100$, wherein C is the percentage of alive insects in untreated controls, and G is the percentage of alive insects in plants treated with components of the ginkgo tree.

Example-1

*Zea mays* plants were grown to growth stage BBCH 12. The maize plants were then sprayed with 300 l/ha of aqueous compositions comprising either no component of the ginkgo tree, 300 ppm of ginkgolide A, or 100 ppm of bilobalide. The plants were then allowed to dry and subsequently infested with five insects (either adult, or $4^{th}$ instar nymphs) of *Nezara viridula*. Insects were contained on the plant using mesh organza bags. Three replicates on different plants were made for each measurement. Three days after infestation, the number of live and dead insects was determined. The mean mortality values were gathered in Table D.

TABLE D

Mortality in percent of *N. viridula* three days after treatment

| Applied Compound | Mortality of Adults [%] | Mortality of $4^{th}$ instar nymphs [%] |
|---|---|---|
| Untreated Control | 0 | 0 |
| Ginkgolide A | 20.0 | 61.5 |
| Bilobalide | 33.3 | 84.6 |

Example-2

Ginkgolide A and Bilobalide were each dissolved in a solution of 50 wt % of acetone in water and applied to the soil of corn four days after planting at a rate of 2.5 mg of the active ingredient per plant. Prior to infestation the soil was covered with parafilm to prevent insect exposure to treated soil. Each plant was infested 3DAT with four $4^{th}$ instar *Nezara viridula* insects. Insects were contained on the plant using organza fabric bags. Four replicates on different plants were made for each measurement. The mortality of the insects was measured 7DAT. The mean mortality values were gathered in Table E.

TABLE E

Mortality in percent of *N. viridula* by soil drench

| Applied Compound | Mortality of $4^{th}$ instar nymphs relative to untreated control [%] |
|---|---|
| Ginkgolide A | 100 |
| Bilobalide | 85 |

Example-3

Ginkgolide A was dissolved in DMSO and applied to corn seeds at rates of 1.0 and 0.5 mg of Ginkgolide A per plant. One seed was planted per pot in a 1:1 mixture of North Carolina loamy sand:sand. Prior to infestation, soil was covered with parafilm to prevent insect exposure to treated soil. After emergence of the plants, each pot was infested with four $4^{th}$ instar *Nezara viridula* insects. Insects were contained on the pots using organza fabric bags. Four replicates on different plants were made for each measurement. The mean damage protection of the corn plants was assessed 10DAT in comparison with untreated controls. For plant height, root mass, and root length, evaluation of the damage protection of the plants was carried out for each treatment as the increase from the infested solvent blank (SB) relative to the increase of the uninfested control from the infested solvent blank: (Treatment−Infested SB)/Uninfested SB−Infested SB)×100%. The results of the mean damage protection values were gathered in Table F.

TABLE F

Mean damage protection in percent of *N. viridula* by seed treatment.

| Rate in mg/seed | Mean damage protection [%] |
| --- | --- |
| 1.0 | 77 |
| 0.5 | 64 |

Example-4

Agrisure™ Viptera and Roundoup Ready™ 2 *Zea mays* seedlings were sprayed with 1 ml of compositions comprising either no component of the ginkgo tree, or bilobalide at a concentration of 50, 100, or 150 ppm. Plants were allowed to dry and subsequently infested with ten adult insects of *Euschistus heros*. Three replicate measurement on different plants were made for each measurement. Six days after infestation (6DAI) number of live and dead insects was determined. The mean number of alive insects, as well as the relative efficacy values (E) according to Abbott's formula were gathered in Table G, wherein the number of alive insects in untreated controls (C) was the value of the same plant without the application of bilobalide.

TABLE G

Control of *E. heros* in corn by bilobalide

| Maize plant | Concentration of bilobalide [ppm] | No of alive insects 6DAI | Relative Efficacy 6DAI [%] |
|---|---|---|---|
| Roundoup Ready ™ 2 | — | 6.0 | — |
| Agrisure ™ Viptera | — | 8.7 | — |
| Roundoup Ready ™ 2 | 150 | 0.3 | 94 |
| Agrisure ™ Viptera | 150 | 0.0 | 100 |
| Roundoup Ready ™ 2 | 100 | 0.7 | 89 |
| Agrisure ™ Viptera | 100 | 0.3 | 96 |
| Roundoup Ready ™ 2 | 50 | 1.0 | 83 |
| Agrisure ™ Viptera | 50 | 0.7 | 92 |

Example-5

The experiment as described in Example-4 was repeated with ginkgolide A in a concentration of 250 ppm. Three days after infestation (3DAI) number of live and dead insects was determined. The mean number of alive insects, as well as the relative efficacy values (E) according to Abbott's formula were gathered in Table H, wherein the number of alive insects in untreated controls (C) was the value of the same plant without the application of ginkgolide A.

TABLE H

Control of *E. heros* in corn by bilobalide

| Maize plant | Concentration of ginkgolide A [ppm] | No of alive insects 3DAI | Relative Efficacy 3DAI [%] |
|---|---|---|---|
| Roundoup Ready ™ 2 | — | 9.7 | — |
| Agrisure ™ Viptera | — | 8.7 | — |
| Roundoup Ready ™ 2 | 250 | 7.7 | 21 |
| Agrisure ™ Viptera | 250 | 5.7 | 35 |
| Roundoup Ready ™ 2 | 10 | 8.3 | 14 |
| Agrisure ™ Viptera | 10 | 5.3 | 38 |

We claim:

1. A method for controlling pests selected from the family of Pentatomidae, Thripidae, or a combination thereof of a genetically modified maize plant having at least one toxin of *Bacillus thuringiensis* formed in the plant, the method comprising contacting the maize plant, parts of the maize plant, or its propagation material with components of a ginkgo tree selected from the group consisting of bilobalide, ginkgolide A, ginkgolide B, ginkgolide C, ginkgolide J and ginkgolide M, and mixtures thereof:

wherein the genetically modified maize plant has at least one toxin of *Bacillus thuringiensis* formed in the plant;

wherein the pests are selected from the family of Pentatomidae, Thripidae, or a combination thereof; and wherein said pests contact said components of a ginkgo tree.

2. The method of claim 1, wherein the pests are from the family of Pentatomidae.

3. The method of claim 1, wherein the pests are one of *Euschistus* spp., *Halyomorpha* spp., *Dichelops* spp., *Nezara* spp., and *Oebalus* spp.

4. The method according to claim 1, wherein the pests are one of *Euschistus servus, Euschistus heros, Halyomorpha halys, Dichelops furcatus, Dichelops melacanthus, Nezara viridula*, and *Oebalus pugnax*.

5. The method according to claim 1, further comprising applying the components of the ginkgo tree using a soil drench treatment.

6. The method according to claim 1, further comprising applying the components of the ginkgo tree using an in-furrow treatment.

7. The method according to claim 1, further comprising applying the components of the ginkgo tree using a foliar application.

8. The method according to claim 1, further comprising applying the components of the ginkgo tree in an amount between about 1 g/Ha and about 500 g/ha.

9. The method according to claim 1, wherein the components of the ginkgo tree are one of ginkgolide A, bilobalide, and a mixture thereof.

10. The method according to claim 1, wherein the maize plant has been modified by mutagenesis or genetic engineering.

11. The method according to claim 1, wherein the genetically modified maize plant has an insect resistance conveyed by a gene selected from the group consisting of cry1Aa, cry1Ab, cry1A.105, cry1F, cry1Fa2, cry2Ab2, cry2Ae, cry3Bb1, cry3Bb1, cry34Ab1, cry35Ab1, cry9c, dvsnf7, ecry3.1Ab, mcry3A, mocry1F, pint, vip3Aa20, and combinations thereof.

12. The method according to claim 1, wherein the genetically modified maize plant has an insect resistance conveyed by a gene selected from the group consisting of cry3Bb1, cry34Ab1, cry35Ab1, ecry3.1Ab, mcry3A, and combinations thereof.

13. The method according to claim 1, wherein the genetically modified maize plant has a herbicide tolerance conveyed by at least one gene selected from the group consisting of pat, mepsps, cp4 epsps, zm-hra, gat4621, aad1, bar, 2mepsps, gov247, epsps grg23ace5, ACCase (mutant), als (mutant), dmo, and combinations thereof.

* * * * *